US012509436B2

(12) United States Patent
Chang et al.

(10) Patent No.: US 12,509,436 B2
(45) Date of Patent: Dec. 30, 2025

(54) BENZAMIDE DERIVATIVES AS CGAS-STING PATHWAY AGONISTS

(71) Applicant: Baruch S. Blumberg Institute, Doylestown, PA (US)

(72) Inventors: Jinhong Chang, Chalfont, PA (US); Yanming Du, Cheshire, CT (US); Ju-Tao Guo, Lansdale, PA (US)

(73) Assignee: BARUCH S. BLUMBERG INSTITUTE, Doylestown, PA (US)

( * ) Notice: Subject to any disclaimer, the term of this patent is extended or adjusted under 35 U.S.C. 154(b) by 894 days.

(21) Appl. No.: 17/282,233

(22) PCT Filed: Oct. 1, 2019

(86) PCT No.: PCT/US2019/054065

§ 371 (c)(1),
(2) Date: Apr. 1, 2021

(87) PCT Pub. No.: WO2020/072492

PCT Pub. Date: Apr. 9, 2020

(65) Prior Publication Data

US 2021/0347752 A1 Nov. 11, 2021

Related U.S. Application Data

(60) Provisional application No. 62/740,210, filed on Oct. 2, 2018.

(51) Int. Cl.

| | |
|---|---|
| ***C07D 317/68*** | (2006.01) |
| ***A61P 35/00*** | (2006.01) |
| ***C07C 233/66*** | (2006.01) |
| ***C07C 235/56*** | (2006.01) |
| ***C07D 213/82*** | (2006.01) |
| ***C07D 319/18*** | (2006.01) |
| ***C07D 321/10*** | (2006.01) |
| ***C07D 405/12*** | (2006.01) |
| ***C07D 417/12*** | (2006.01) |

(52) U.S. Cl.

CPC ............ *C07D 317/68* (2013.01); *A61P 35/00* (2018.01); *C07C 233/66* (2013.01); *C07C 235/56* (2013.01); *C07D 213/82* (2013.01); *C07D 319/18* (2013.01); *C07D 321/10* (2013.01); *C07D 405/12* (2013.01); *C07D 417/12* (2013.01); *C07C 2602/10* (2017.05)

(58) Field of Classification Search

CPC .. C07D 317/68; C07D 213/82; C07D 319/18; C07D 321/10; C07D 405/12; C07D 417/12; C07D 231/56; C07D 241/24; C07D 405/06; A61P 35/00; C07C 233/66; C07C 235/56; C07C 2602/10; C07C 2602/08; C07C 233/65

See application file for complete search history.

(56) References Cited

U.S. PATENT DOCUMENTS

| | | | |
|---|---|---|---|
| 2,786,048 A | 3/1957 | Schwyzer | |
| 3,340,042 A * | 9/1967 | Schwartz | C07F 9/74 504/315 |
| 3,981,814 A | 9/1976 | Nikawitz | |
| 4,659,738 A | 4/1987 | Miller et al. | |

OTHER PUBLICATIONS

National Center for Biotechnology Information. PubChem Compound Summary for CID 325108, 6-bromo-N-naphthalene-1-yl-1,3-benzodioxole-5-carboxamide. https://pubchem.ncbi.nlm.nih.gov/compound/325108, Created Mar. 26, 2005; Accessed Feb. 29, 2024. (Year: 2005).*

National Center for Biotechnology Information. PubChem Bioassay Record for AID 504832, Source: National Center for Advancing Translational Sciences (NCATS). https://pubchem.ncbi.nlm.nih.gov/bioassay/504832. Deposited Jun. 22, 2011; Accessed Feb. 29, 2024 (Year: 2011).*

Kagechika et al. Retinobenzoic Acids. 1. Structure-Activity Relationships of Aromatic Amides with Retinoidal Activity, (Journal of Medicinal Chemistry, 31:11, p. 2182-2192). (Year: 1988).*

CAS Registry No. 63295-62-5. (Year: 1984).*

CAS Registry No. 119899-28-4 (Year: 1989).*

Zhu et al. N-(naphthalen-1-yl)benzamide (Acta Cryst. E67, o3204). (Year: 2011).*

CAS Registry No. 339267-17-3 (which entered the STN database on Jun. 4, 2001). (Year: 2001).*

Pubmed Compound Summary for CID 21807113, '5-Pyrim'dinecarboxamide ,n-phenyl-', U.S. National Library of Medicine,Dec. 5, 2007 (Dec. 5, 2007), p. 1-10; p. 2 (https://pubchem.ncbi.nlm.nih.gov/compound/21807113).

* cited by examiner

*Primary Examiner* — Joseph K Mckane
*Assistant Examiner* — Meghan C Heasley
(74) *Attorney, Agent, or Firm* — The Belles Group, P.C.

(57) ABSTRACT

Pharmaceutical compositions of the invention comprise functionalized benzamide derivatives useful as cyclic GMP-AMP synthase-Stimulator of interferon gene (cGAS-STING) pathway agonists, and useful for treating viral diseases and boost antitumor immunity.

10 Claims, No Drawings

BENZAMIDE DERIVATIVES AS CGAS-STING PATHWAY AGONISTS

CROSS-REFERNCE TO RELATED APPLICATION

The present application is a National Stage Entry of PCT/US19/54065, filed Oct. 1, 2019, which in turn claims the benefit of priority from U.S. Provisional Application No. 62/740,210, filed Oct. 2, 2018; the contents of which are hereby incorporated herein by reference in their entireties.

BACKGROUND

The genomes of vertebrate animals encode an array of proteins called pattern recognition receptors (PRRs) that recognize pathogen associated molecular patterns upon infection of microorganisms to activate a proinflammatory cytokine response (Akira et al., 2006). This innate cytokine response not only inhibits the proliferation and limits the spread of the microorganisms, but also orchestrates the induction of more powerful adaptive immune response to ultimately control the microorganism infections (Chang et al., 2012; Iwasaki and Medzhitov, 2015). Stimulator of interferon gene (STING) is a transmembrane protein localized in the membrane of endoplasmic reticulum (ER) and serves as a PRR for cyclic dinucleotides produced by intracellular bacteria or synthesized by the cytoplasmic DNA sensor, cyclic GMP-AMP synthase (cGAS) (Sun et al., 2013; Wu et al., 2013). Binding of the cyclic dinucleotides to STING induces its dimerization and translocation from ER membrane to perinuclear vesicles and subsequently activates NFkB and TBK-1/IRF3 (Burdette et al., 2011; Yin et al., 2012). Activation of these signaling pathways induces the expression of type I and type III interferons as well as other inflammatory cytokines (Tanaka and Chen, 2012). In addition, STING also serves as the adaptor for several other cytoplasmic and nuclear PRRs that recognize DNA to activate innate immune responses (Chen et al., 2016; Kondo et al., 2013). Therefore, STING is a molecular hub for DNA activation of innate immune response and has been demonstrated to play an essential role in host defense against the infection of DNA viruses, retroviruses, intracellular bacteria and protozoa (Cai et al., 2014). Moreover, accumulating evidence suggests that STING also play an important role in host anti-tumor immunity (Corrales et al., 2016).

Due to its critical role in host immune responses, pharmacological modulation of STING activity has been considered as a viable broad spectrum immunotherapeutic approach for treatment of pathogen infections and tumors. Indeed, recent studies showed that intra-tumor administration of 2'3'-cGAMP induced profound regression of established tumors in mice and generated substantial systemic immune responses capable of rejecting distant metastases and providing long-lived immunologic memory (Corrales et al., 2015; Iurescia et al., 2018). STING agonists had also been demonstrated to potentiate the efficacy of immune checkpoint blockade therapy (Ghaffari et al., 2018; Wang et al., 2017) and enhance the immunogenicity of vaccines (Fu et al., 2015; Hanson et al., 2015). In addition, we and others demonstrated that STING agonist therapy were able to induce a host immune response to control the infection of influenza A virus (Shirey et al., 2011), hepatitis B virus (HBV) (Guo et al., 2015; Guo et al., 2017), herpes simplex virus (HSV) (Skouboe et al., 2018) and human immunodeficiency virus (HIV) (Aroh et al., 2017). These studies prove the concept that pharmacologic activation of STING is an attractive immunotherapeutic approach to treat viral infection and cancers.

Additional chronic viral infections that may be treated by activation of STING include Hepatitis C virus (HCV), as well as DNA and RNA viruses causing acute infections, such as influenza viruses and other families of viruses that cause the common cold and upper respiratory tract infections including but not limited to Paramyxoviruses, Rhinoviruses, Adenoviruses, Human Coronaviruses (including severe respiratory syndrome associated coronavirus; middle east respiratory syndrome coronavirus, and Human coronavirus OC43), families of viruses that cause hemorrhagic fever (including but not limited to viruses belong to flaviviridae, filoviridae, arenaviridae, and bunyaviridae), and viruses that cause encephalitis (including but not limited to West Nile virus, LaCrosse virus, California encephalitis virus, Venezuelan equine encephalitis virus, western equine encephalitis, Japanese encephalitis virus, Kyasanur forest virus, Tick-borne encephalitis virus, rabies virus, Chikungunya virus).

Cancers that may be treated by activation of STING include bladder cancer, breast cancer, colorectal cancer, kidney cancer liver cancer, lung cancer, melanoma, oral and oropharyngeal cancer, pancreatic cancer, prostate cancer, thyroid cancer, uterine cancer, leukemia and lymphoma.

Currently, there are two classes of STING agonists, cyclic dinucleotides (CDNs) and non-nucleotide small molecules. Bacterial produced cyclic-di-GMP and cyclic-di-AMP are the first identified STING agonists (Burdette et al., 2011). With the discovery of cytosolic DNA sensor cGAS, its catalytic product 2',3'-cGAMP was identified as an even more potent STING agonist (Zhang et al., 2013). Although the various formulations of CDNs have been demonstrated to facilitate the activation of antitumor immune response in mouse models (Fu et al., 2015), their poor cell membrane permeability and metabolic instability may limit their biological activity and medical applications. Accordingly, medicinal chemistry efforts have been made to produce novel CDNs that are resistant to the degradation of cellular ecto-nucleotide pyrophosphatase/phosphodiesterase (ENPP1) (Li et al., 2014; Lioux et al., 2016). In addition, delivery of CDNs with nanoparticles or liposome improved their antitumor activities in vivo (Hanson et al., 2015). So far, there are only four chemotypes of non-nucleotide small molecular STING agonists, DMXAA, G10, C11 and DSDP. 5,6-dimethylxanthenone-4-acetic acid (DMXAA) was initially discovered and developed as a vascular disrupting agent with antitumor activity in various mouse models, but failed in phase III clinical trials for treatment of lung cancer (Conlon et al., 2013). It was recently identified to be a specific agonist of mouse STING and induced an interferon (IFN)-dominant cytokine response to potently inhibit the replication of influenza A virus, hepatitis B virus and also alphavirus in mice (Caviar et al., 2013; Conlon et al., 2013; Guo et al., 2015). Interestingly, a genetic study revealed that a single amino acid substitution (S162A) in human STING confers DMXAA sensitivity, which provides a clue for the synthesis of DMXAA analogues as human STING agonists (Gao et al., 2013). G10, or 4-(2-chloro-6-fluorobenzyl)-N-(furan-2-ylmethyl)-3-oxo-3,4-dihydro-2H-benzo[b][1,4]thiazine-6-carboxamide, and C11, or N-(methylcarbamoyl)-2-{[5-(4-methylphenyl)-1,3,4-oxadiazol-2-yl]sulfanyl}-2-phenylacetamide, are two recently identified human STING-specific agonist by high throughput screening from Victor R. DeFilippis group. Both G10 and C11 had been demonstrated to induce an antiviral response in human fibroblasts against alphaviruses. DSDP, or dispiro diketopiperzine compound, 2,7,2",2"-dispiro[indene-1",3"-dione]-tetrahydrodithiazolo [3,2-a:3',2'-d]pyrazine-5,10(5aH, 10aH)-dione, is another human SITNG specific agonist identified by the inventors' groups with antiviral activities against several flavivirus including dengue virus, yellow fever virus and zika virus. However, these three small molecule human STING agonists' in vivo biological activity and pharmacological property remain to be determined (Liu et al., 2017)(Sali et al., 2015).

Thus, there remains a need for more effective small molecular STING agonists with favorable pharmacological properties as the candidates of immunotherapeutics for viral diseases and cancers. The invention provides compounds that are cGAS-STING pathway agonists, which can induce proinflammatory cytokine response in a human STING-dependent manner.

SUMMARY

The present invention is directed towards functionalized benzamide derivatives of the formula (I):

(I)

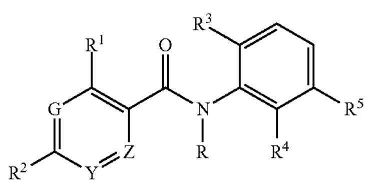

including hydrates, solvates, pharmaceutically acceptable salts, prodrugs and complexes thereof, wherein:

G, Y, and Z are selected from a group consisting of $CR^6$ and N; or one of G, Y, and Z absent and the adjacent atoms are joined together to form a 5-membered ring.

R is selected from the group consisting of hydrogen and $C_{1-6}$ alkyl;

$R^1$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

$R^2$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

$R^3$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

$R^4$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

R and $R^4$ are taken together to with the atoms to which they are bound to form a ring having 5 to 8 members optionally containing a moiety selected from the group consisting of oxygen, C═O, and $SO_2$;

$R^5$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

$R^6$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

R and $R^6$ are taken together to with the atoms to which they are bound to form a ring having 5 to 8 members;

$R^1$ and $R^6$ are taken together with the atom to which they are bound to form an optionally substituted ring having 5-7 ring atoms;

$R^2$ and $R^6$ are taken together with the atom to which they are bound to form an optionally substituted ring having 5-7 ring atoms;

$R^2$ and $R^6$ are taken together with the atom to which they are bound to form an optionally substituted aromatic ring having 5-6 ring atoms, optionally containing a moiety selected from oxygen, sulfur, nitrogen, and NH;

$R^4$ and $R^5$ are taken together with the atom to which they are bound to form an optionally substituted ring having 5-7 ring atoms optionally containing a moiety selected from oxygen, sulfur, nitrogen, and NH;

$R^4$ and $R^5$ are taken together with the atom to which they are bound to form an optionally substituted aromatic ring having 5-6 ring atoms, optionally containing zero to three moieties selected from oxygen, sulfur, nitrogen, and NH;

$R^7$ is selected from a group consisting of hydrogen, optionally substituted $C_{1-4}$ alkyl, optionally substituted $C_3$-$C_7$ cycloalkyl, and optionally substituted phenyl;

$R^8$ is selected from a group consisting of hydrogen, optionally substituted $C_{1-4}$ alkyl, optionally substituted $C_3$-$C_7$ cycloalkyl, and optionally substituted phenyl;

$R^9$ is selected from a group consisting of hydrogen, optionally substituted $C_{1-4}$ alkyl, optionally substituted $C_3$-$C_7$ cycloalkyl, and optionally substituted phenyl, optionally substituted heteroaryl, $COR^{10}$, $SO_2R^{10}$;

$R^{10}$ is selected from a group consisting of hydrogen, optionally substituted $C_{1-4}$ alkyl, optionally substituted $C_3$-$C_7$ cycloalkyl, and optionally substituted phenyl;

$R^9$ and $R^{10}$ units are taken together with the atoms to which they are bound to form a ring having 5-8 ring atoms;

Two $R^{10}$ units are taken together with the atoms to which they are bound to form a ring having 5-8 ring atoms;

$R^{11}$ is selected from a group consisting of hydrogen, optionally substituted $C_{1-4}$ alkyl, optionally substituted $C_3$-$C_7$ cycloalkyl, and optionally substituted phenyl.

In some embodiments, the compounds are useful as cyclic GMP-AMP synthase-stimulators of interferon gene (cGAS-STING) pathway agonists, for treating viral diseases and boost antitumor immunity.

The compounds of the present invention include compounds having formula (II):

(II)

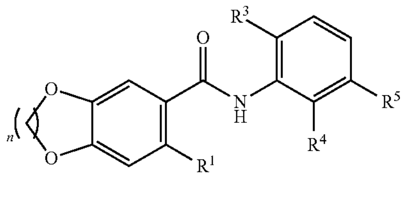

including hydrates, solvates, pharmaceutically acceptable salts, prodrugs and complexes thereof wherein:

n is 1 or 2 or 3; and $R^1$, $R^3$, $R^4$ and $R^5$ are as defined elsewhere herein.

The compounds of the present invention include compounds having formula (III):

(III)

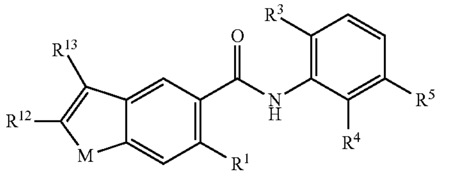

including hydrates, solvates, pharmaceutically acceptable salts, prodrugs and complexes thereof, wherein:

$R^{12}$ is selected from a group consisting of hydrogen, halogen, optionally substituted $C_{1-6}$ haloalkyl, optionally substituted $C_{1-6}$ alkenyl, $CO_2R^7$, $CONHR^8$, $NHCOR^9$, $OR^{10}$, cyano, $N_3$, $SO_2R^{11}$, optionally substituted phenyl, optionally substituted heteroaryl, and N-containing monocyclic heterocycloalkyl;

$R^{13}$ is selected from a group consisting of hydrogen, halogen, optionally substituted $C_{1-6}$ haloalkyl, optionally substituted $C_{1-6}$ alkenyl, $CO_2R^7$, $CONHR^8$, $NHCOR^9$, $OR^{10}$, cyano, $N_3$, $SO_2R^{11}$, optionally substituted phenyl, optionally substituted heteroaryl, and N-containing monocyclic heterocycloalkyl; and M is selected from a group consisting of O, S, and NH;

The compounds of the present invention include compounds having formula (IV):

(IV)

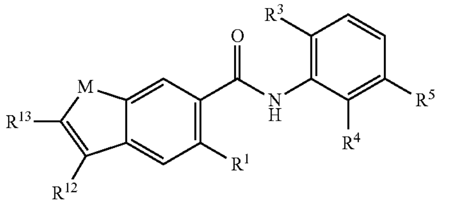

including hydrates, solvates, pharmaceutically acceptable salts, prodrugs and complexes thereof, wherein:

$R^{12}$ is selected from a group consisting of hydrogen, halogen, optionally substituted $C_{1-6}$ haloalkyl, optionally substituted $C_{1-6}$ alkenyl, $CO_2R^7$, $CONHR^8$, $NHCOR^9$, $OR^{10}$, cyano, $N_3$, $SO_2R^{11}$, optionally substituted phenyl, optionally substituted heteroaryl, and N-containing monocyclic heterocycloalkyl;

$R^{13}$ is selected from a group consisting of hydrogen, halogen, optionally substituted $C_{1-6}$ haloalkyl, optionally substituted $C_{1-6}$ alkenyl, $CO_2R^7$, $CONHR^8$, $NHCOR^9$, $OR^{10}$, cyano, $N_3$, $SO_2R^{11}$, optionally substituted phenyl, optionally substituted heteroaryl, and N-containing monocyclic heterocycloalkyl; and M is selected from a group consisting of O, S, and NH.

The compounds of the present invention include compounds having formula (V):

(V)

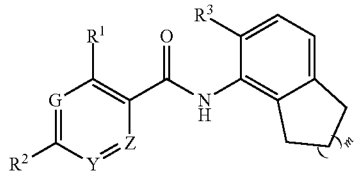

including hydrates, solvates, pharmaceutically acceptable salts, prodrugs and complexes thereof, wherein:

m is 1, 2 or 3; and $R^1$, $R^2$ and $R^3$ are as defined elsewhere herein.

The compounds of the present invention include compounds having formula (VI):

(VI)

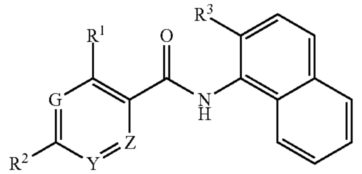

including hydrates, solvates, pharmaceutically acceptable salts, prodrugs and complexes thereof, wherein $R^1$, $R^2$ and $R^3$ are as defined elsewhere herein.

The compounds of the present invention include compounds having formula (VII):

(VII)

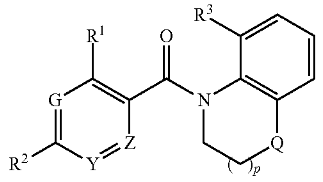

including hydrates, solvates, pharmaceutically acceptable salts, prodrugs and complexes thereof, wherein:

p is 0, 1, 2 or 3;

Q is selected from a group consisting of $CH_2$, O, C═O, $SO_2$; and $R^1$, $R^2$ and $R^3$ are as defined elsewhere herein.

The compounds of the present invention include compounds having formula (VIII):

(VIII)

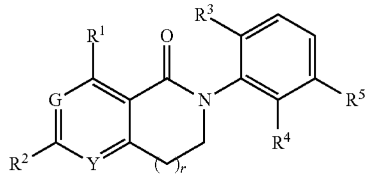

including hydrates, solvates, pharmaceutically acceptable salts, prodrugs and complexes thereof, wherein:

r is 0, 1, 2 or 3; and $R^1$, $R^2$, $R^3$, $R^4$ and $R^5$ are as defined elsewhere herein.

The compounds of the present invention include compounds having formula (IX):

(IX)

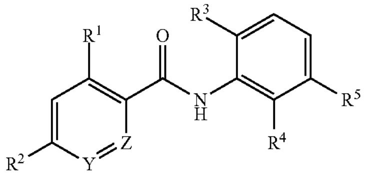

including hydrates, solvates, pharmaceutically acceptable salts, prodrugs and complexes thereof, wherein:

Y, Z, $R^1$, $R^2$, $R^3$, $R^4$ and $R^5$ are as defined elsewhere herein.

The compounds of the present invention include compounds having formula (X):

(X)

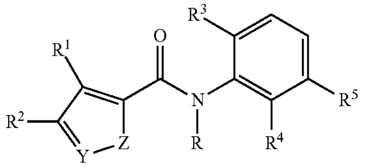

including hydrates, solvates, pharmaceutically acceptable salts, prodrugs and complexes thereof, wherein:

Y, Z, R, $R^1$, $R^2$, $R^3$, $R^4$ and $R^5$ are as defined elsewhere herein.

The compounds of the present invention include compounds having formula (XI):

(XI)

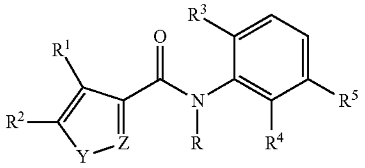

including hydrates, solvates, pharmaceutically acceptable salts, prodrugs and complexes thereof, wherein:

Y, Z, R, $R^1$, $R^2$, $R^3$, $R^4$ and $R^5$ are as defined elsewhere herein.

The compounds of the present invention include compounds having formula (XII):

(XII)

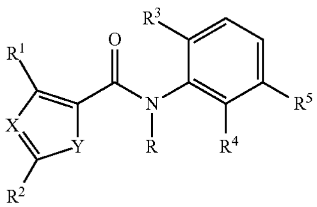

including hydrates, solvates, pharmaceutically acceptable salts, prodrugs and complexes thereof, wherein:

X, Y, R, $R^1$, $R^2$, $R^3$, $R^4$ and $R^5$ are as defined elsewhere herein.

The compounds of the present invention include compounds having formula (XIII):

(XIII)

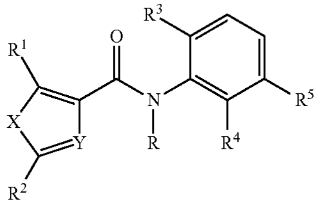

including hydrates, solvates, pharmaceutically acceptable salts, prodrugs and complexes thereof, wherein:

X, Y, R, $R^1$, $R^2$, $R^3$, $R^4$ and $R^5$ are as defined elsewhere herein.

In preferred embodiments the N-containing monocyclic heterocycloalkyl is selected from the group consisting of

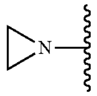 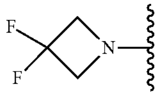, 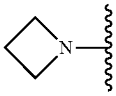,

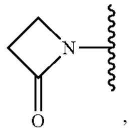, 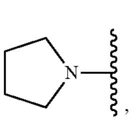, 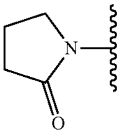,

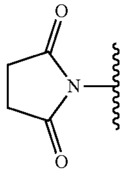, 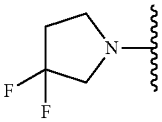, 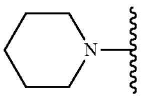,

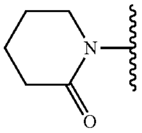, 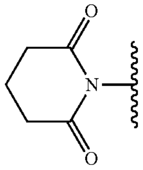,

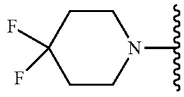, 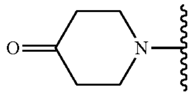, and

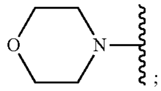;

Embodiments of the present invention further relate to compositions comprising an effective amount of one or more compounds according to the present invention and an excipient.

The present invention also relates to a method for treating or preventing diseases that involve cyclic GMP-AMP synthase-Stimulator of interferon gene (cGAS-STING) pathway agonists, and useful for treating viral diseases and boost antitumor immunity, including, for example, HBV infection, said method comprising administering to a subject an effective amount of a compound or composition according to the present invention.

The present invention yet further relates to a method for treating or preventing diseases that involve cyclic GMP-AMP synthase-Stimulator of interferon gene (cGAS-STING) pathway agonists, and useful for treating viral diseases and boost antitumor immunity, including, for example, HBV infection, wherein said method comprises administering to a subject a composition comprising an effective amount of one or more compounds according to the present invention and an excipient.

The present invention also relates to a method for treating or preventing disease or conditions associated with HBV infection, and diseases that involve cyclic GMP-AMP synthase-Stimulator of interferon gene (cGAS-STING) pathway agonists, and useful for treating viral diseases and boost antitumor immunity, said method comprise administering to a subject an effective amount of a compound or composition according to the present invention.

The present invention yet further relates to a method for treating or preventing disease or conditions associated with HBV infection, and diseases that involve cyclic GMP-AMP synthase-Stimulator of interferon gene (cGAS-STING) pathway agonists, and useful for treating viral diseases and boost antitumor immunity, wherein said method comprises administering to a subject a composition comprising an effective amount of one or more compounds according to the present invention and an excipient.

The present invention also relates to a method for treating or preventing chronic viral infection caused by Hepatitis C virus (HCV), herpes simplex virus (HSV), human immunodeficiency virus (HIV), as well as DNA and RNA viruses causing acute infections such as influenza viruses and other families of viruses that cause the common cold and upper respiratory tract infections including but not limited to Paramyxoviruses, Rhinoviruses, Adenoviruses, Human Coronaviruses (including severe respiratory syndrome associated coronavirus; middle east respiratory syndrome coronavirus, and Human coronavirus OC43), families of viruses that cause hemorrhagic fever (including but not limited to viruses belong to flaviviridae, filoviridae, arenaviridae, and bunyaviridae), and viruses that cause encephalitis (including but not limited to West Nile virus, LaCrosse virus, California encephalitis virus, Venezuelan equine encephalitis virus, western equine encephalitis, Japanese encephalitis virus, Kyasanur forest virus, Tickborne encephalitis virus, rabies virus, Chikungunya virus), said method comprise administering to a subject an effective amount of a compound or composition according to the present invention.

The present invention yet further relates to a method for treating or preventing disease or conditions associated with chronic viral infection caused by Hepatitis C virus (HCV), herpes simplex virus (HSV), as well as DNA and RNA viruses causing acute infections such as influenza viruses and other families of viruses that cause the common cold and upper respiratory tract infections including but not limited to Paramyxoviruses, Rhinoviruses, Adenoviruses, Human Coronaviruses (including severe respiratory syndrome associated coronavirus; middle east respiratory syndrome coronavirus, and Human coronavirus OC43), families of viruses that cause hemorrhagic fever (including but not limited to viruses belong to flaviviridae, filoviridae, arenaviridae, and bunyaviridae), and viruses that cause encephalitis (including but not limited to West Nile virus, LaCrosse virus, California encephalitis virus, Venezuelan equine encephalitis virus, western equine encephalitis, Japanese encephalitis virus, Kyasanur forest virus, Tickborne encephalitis virus, rabies virus, Chikungunya virus), said method comprise administering to a subject an effective amount of a compound or composition according to the present invention.

The present invention also relates to a method for treating or preventing cancer including bladder cancer, breast cancer, colorectal cancer, kidney cancer liver cancer, lung cancer, melanoma, oral and oropharyngeal cancer, pancreatic cancer, prostate cancer, thyroid cancer, uterine cancer, leukemia and lymphoma, said method comprise administering to a subject an effective amount of a compound or composition according to the present invention.

The present invention yet further relates to a method for treating or preventing disease or conditions associated with cancer including bladder cancer, breast cancer, colorectal cancer, kidney cancer liver cancer, lung cancer, melanoma, oral and oropharyngeal cancer, pancreatic cancer, prostate cancer, thyroid cancer, uterine cancer, leukemia and lymphoma, said method comprise administering to a subject an effective amount of a compound or composition according to the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, isobutyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2amino$, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo [3.1.1]heptanyl, 1,3-dimethyl[2.2.1]heptan-2-yl, bicyclo [2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1H-pyrrole, 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

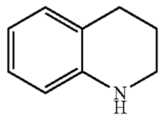

is, for the purposes of the present invention, considered a heterocyclic unit. 6,7-Dihydro-5H-cyclopentapyrimidine having the formula:

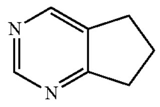

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

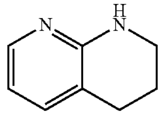

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —$NO_2$, oxo (═O), —$OR^{14}$, —$SR^{14}$, —$N(R^{14})_2$, —$NR^{14}C(O)R^{14}$, —$SO_2R^{14}$, —$SO_2OR^{14}$, —$SO_2N(R^{14})_2$, —$C(O)R^{14}$, —$C(O)OR^{14}$, —$C(O)N(R^{14})_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —$NO_2$, oxo, and $R^{14}$; wherein $R^{14}$, at each occurrence, independently is hydrogen, —$OR^{15}$, —$SR^{15}$, —$C(O)R^{15}$, —$C(O)OR^{15}$, —$C(O)N(R^{15})_2$, —$SO_2R^{15}$, —$S(O)_2OR^{15}$, —$N(R^{15})_2$, —$NR^{15}C(O)R^{15}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{14}$ units taken together with the atom(s) to which they are bound form an optionally substituted carbocycle or heterocycle wherein said carbocycle or heterocycle has 3 to 7 ring atoms; wherein $R^{15}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{15}$ units taken together with the atom(s) to which they are bound form an optionally substituted carbocycle or heterocycle wherein said carbocycle or heterocycle preferably has 3 to 7 ring atoms.

In some embodiments, the substituents are selected from:

i) —$OR^{16}$; for example, —OH, —$OCH_3$, —$OCH_2CH_3$, —$OCH_2CH_2CH_3$;

ii) —$C(O)R^{16}$; for example, —$COCH_3$, —$COCH_2CH_3$, —$COCH_2CH_2CH_3$;

iii) —$C(O)OR^{16}$; for example, —$CO_2CH_3$, —$CO_2CH_2CH_3$, —$CO_2CH_2CH_2CH_3$;

iv) —$C(O)N(R^{16})_2$; for example, —$CONH_2$, —$CONHCH_3$, —$CON(CH_3)_2$;

v) —$N(R^{16})_2$; for example, —$NH_2$, —$NHCH_3$, —$N(CH_3)_2$, —$NH(CH_2CH_3)$;

vi) halogen: —F, —Cl, —Br, and —I;

vii) —$CH_eX_g$; wherein X is halogen, m is from 0 to 2, e+g=3; for example, —$CH_2F$, —$CHF_2$, —$CF_3$, —$CCl_3$, or —$CBr_2$;

viii) —$SO_2R^{16}$; for example, —$SO_2H$; —$SO_2C_6H_5$;

ix) $C_1$-$C_6$ linear, branched, or cyclic alkyl;

x) Cyano xi) Nitro;

xii) $N(R^{16})C(O)R^{16}$;

xiii) Oxo (=O);

xiv) Fleterocycle; and xv) Fleteroaryl.

wherein each $R^{16}$ is independently hydrogen, optionally substituted CVO, linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^{16}$ units can be taken together to form a ring comprising 3-7 ring atoms. In certain aspects, each $R^{16}$ is independently hydrogen, CVO, linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_1$-$C_6$, $C_1$-$C_5$, $C_1$-$C_4$, $C_1$-$C_3$, $C_1$- $C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the cyclic GMP-AMP synthase-Stimulator of interferon gene (cGAS-STING) pathway agonists described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The cyclic GMP-AMP synthase-Stimulator of interferon gene (cGAS-STING) pathway agonists of the present invention are functionalized benzamide derivatives of the formula (I):

(I)

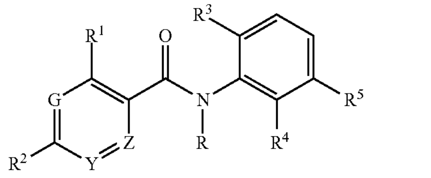

including hydrates, solvates, pharmaceutically acceptable salts, prodrugs and complexes thereof, wherein:

G, Y, and Z are selected from a group consisting of $CR^6$ and N; or one of G, Y, and Z absent and the adjacent atoms are joined together to form a 5 membered ring;

R is selected from the group consisting of hydrogen and $C_{1-6}$ alkyl;

$R^1$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

$R^2$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

$R^3$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

$R^4$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

R and $R^4$ are taken together to with the atoms to which they are bound to form a ring having 5 to 8 members optionally containing a moiety selected from the group consisting of oxygen, C═O, and $SO_2$;

$R^5$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

$R^6$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

R and $R^6$ are taken together to with the atoms to which they are bound to form a ring having 5 to 8 members;

$R^1$ and $R^6$ are taken together with the atom to which they are bound to form an optionally substituted ring having 5-7 ring atoms;

$R^2$ and $R^6$ are taken together with the atom to which they are bound to form an optionally substituted ring having 5-7 ring atoms;

$R^2$ and $R^6$ are taken together with the atom to which they are bound to form an optionally substituted aromatic ring having 5-6 ring atoms, optionally containing a moiety selected from oxygen, sulfur, nitrogen, and NH;

$R^4$ and $R^5$ are taken together with the atom to which they are bound to form an optionally substituted ring having 5-7 ring atoms optionally containing a moiety selected from oxygen, sulfur, nitrogen, and NH;

$R^4$ and $R^5$ are taken together with the atom to which they are bound to form an optionally substituted, optionally aromatic ring having 5-6 ring atoms, optionally containing zero to three moieties selected from oxygen, sulfur, nitrogen, and NH;

$R^7$ is selected from a group consisting of hydrogen, optionally substituted $C_{1-4}$ alkyl, optionally substituted $C_3$-$C_7$ cycloalkyl, and optionally substituted phenyl;

$R^8$ is selected from a group consisting of hydrogen, optionally substituted $C_{1-4}$ alkyl, optionally substituted $C_3$-$C_7$ cycloalkyl, and optionally substituted phenyl;

$R^9$ is selected from a group consisting of hydrogen, optionally substituted $C_{1-4}$ alkyl, optionally substituted $C_3$-$C_7$ cycloalkyl, and optionally substituted phenyl, optionally substituted heteroaryl, $COR^{10}$, and $SO_2R^{10}$;

$R^{10}$ is selected from a group consisting of hydrogen, optionally substituted $C_{1-4}$ alkyl, optionally substituted $C_3$-$C_7$ cycloalkyl, and optionally substituted phenyl;

$R^9$ and $R^{10}$ units are taken together with the atoms to which they are bound to form a ring having 5-8 ring atoms;

two $R^{10}$ units are taken together with the atoms to which they are bound to form a ring having 5-8 ring atoms;

$R^{11}$ is selected from a group consisting of hydrogen, optionally substituted $C_{1-4}$ alkyl, optionally substituted $C_3$-$C_7$ cycloalkyl, and optionally substituted phenyl.

The compounds of the present invention include compounds having formula (II):

(II)

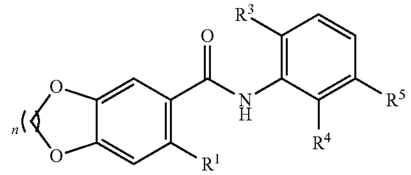

including hydrates, solvates, pharmaceutically acceptable salts, prodrugs and complexes thereof wherein:

n is 1 or 2 or 3; and $R^1$, $R^3$, $R^4$ and $R^5$ are as defined elsewhere herein.

The compounds of the present invention include compounds having formula (III):

(III)

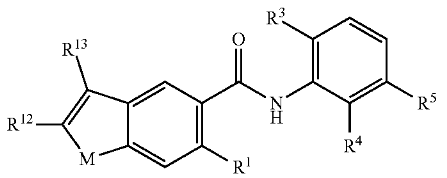

including hydrates, solvates, pharmaceutically acceptable salts, prodrugs and complexes thereof, wherein:

$R^{12}$ is selected from a group consisting of hydrogen, halogen, optionally substituted $C_{1-6}$ haloalkyl, optionally substituted $C_{1-6}$ alkenyl, $CO_2R^7$, $CONHR^8$, $NHCOR^9$, $OR^{10}$, cyano, $N_3$, $SO_2R^{11}$, optionally substituted phenyl, optionally substituted heteroaryl, and N-containing monocyclic heterocycloalkyl;

$R^{13}$ is selected from a group consisting of hydrogen, halogen, optionally substituted $C_{1-6}$ haloalkyl, optionally substituted $C_{1-6}$ alkenyl, $CO_2R^7$, $CONHR^8$, $NHCOR^9$, $OR^{10}$, cyano, $N_3$, $SO_2R^{11}$, optionally substituted phenyl, optionally substituted heteroaryl, and N-containing monocyclic heterocycloalkyl; and M is selected from a group consisting of O, S, and NH; and $R^1$, $R^3$, $R^4$ and $R^5$ are as defined elsewhere herein.

The compounds of the present invention include compounds having formula (IV):

(IV)

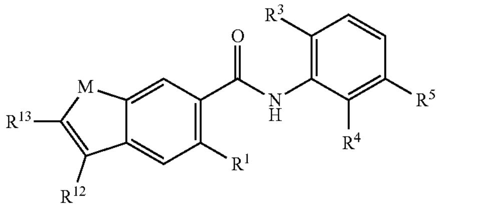

including hydrates, solvates, pharmaceutically acceptable salts, prodrugs and complexes thereof, wherein:

$R^{12}$ is selected from a group consisting of hydrogen, halogen, optionally substituted $C_{1-6}$ haloalkyl, optionally substituted $C_{1-6}$ alkenyl, $CO_2R^7$, $CONHR^8$, $NHCOR^9$, $OR^{10}$, cyano, $N_3$, $SO_2R^{11}$, optionally substituted phenyl, optionally substituted heteroaryl, and N-containing monocyclic heterocycloalkyl;

$R^{13}$ is selected from a group consisting of hydrogen, halogen, optionally substituted $C_{1-6}$ haloalkyl, optionally substituted $C_{1-6}$ alkenyl, $CO_2R^7$, $CONHR^8$, $NHCOR^9$, $OR^{10}$, cyano, $N_3$, $SO_2R^{11}$, optionally substituted phenyl, optionally substituted heteroaryl, and N-containing monocyclic heterocycloalkyl;

M is selected from a group consisting of O, S, and NH; and $R^1$, $R^3$, $R^4$ and $R^5$ are as defined elsewhere herein.

The compounds of the present invention include compounds having formula (V):

(V)

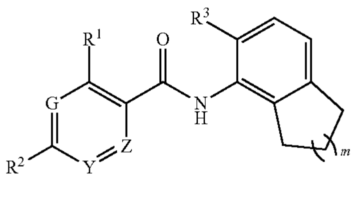

including hydrates, solvates, pharmaceutically acceptable salts, prodrugs and complexes thereof, wherein:

m is 1-3; and $R^1$, $R^2$ and $R^3$ are as defined elsewhere herein.

The compounds of the present invention include compounds having formula (VI):

(VI)

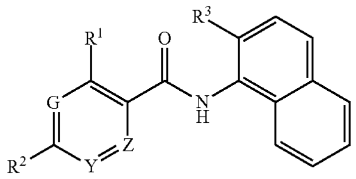

including hydrates, solvates, pharmaceutically acceptable salts, prodrugs and complexes thereof, wherein:

Y, Z, $R^1$, $R^2$ and $R^3$ are as defined elsewhere herein.

The compounds of the present invention include compounds having formula (VII):

(VII)

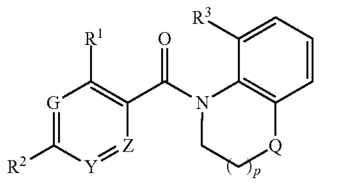

including hydrates, solvates, pharmaceutically acceptable salts, prodrugs and complexes thereof, wherein:

p is 0, 1, 2 or 3;

Q is selected from a group consisting of $CH_2$, O, C═O, $SO_2$; and

Y, Z, $R^1$, $R^2$ and $R^3$ are as defined elsewhere herein.

The compounds of the present invention include compounds having formula (VIII):

(VIII)

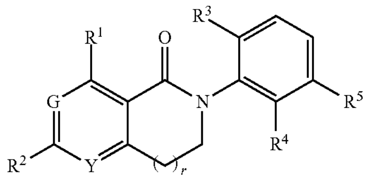

including hydrates, solvates, pharmaceutically acceptable salts, prodrugs and complexes thereof, wherein:

r is 0, 1, 2 or 3; and

G, Y, $R^1$, $R^2$ $R^3$, $R^4$ and $R^5$ are as defined elsewhere herein.

The compounds of the present invention include compounds having formula (IX):

(IX)

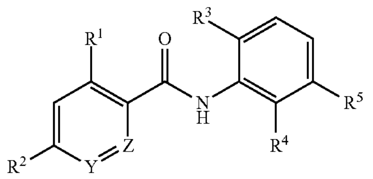

including hydrates, solvates, pharmaceutically acceptable salts, prodrugs and complexes thereof, wherein:

Y, Z, $R^1$, $R^2$ $R^3$, $R^4$ and $R^5$ are as defined elsewhere herein.

The compounds of the present invention include compounds having formula (X):

(X)

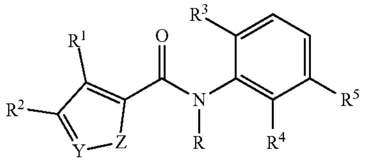

including hydrates, solvates, pharmaceutically acceptable salts, prodrugs and complexes thereof, wherein:

Y, Z, R, $R^1$, $R^2$ $R^3$, $R^4$ and $R^5$ are as defined elsewhere herein.

The compounds of the present invention include compounds having formula (XI):

(XI)

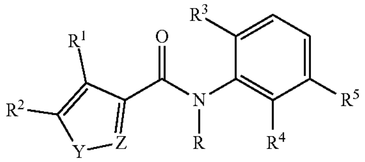

including hydrates, solvates, pharmaceutically acceptable salts, prodrugs and complexes thereof, wherein:

Y, Z, R, $R^1$, $R^2$ $R^3$, $R^4$ and $R^5$ are as defined elsewhere herein.

The compounds of the present invention include compounds having formula (XII):

(XII)

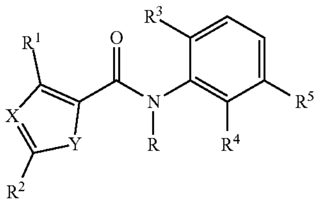

including hydrates, solvates, pharmaceutically acceptable salts, prodrugs and complexes thereof, wherein:

X, Y, R, $R^1$, $R^2$ $R^3$, $R^4$ and $R^5$ are as defined elsewhere herein.

The compounds of the present invention include compounds having formula (XII):

(XIII)

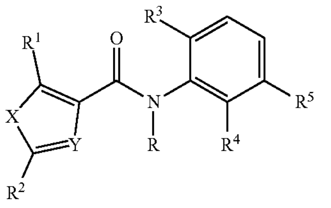

including hydrates, solvates, pharmaceutically acceptable salts, prodrugs and complexes thereof, wherein:

X, Y, R, $R^1$, $R^2$ $R^3$, $R^4$ and $R^5$ are as defined elsewhere herein.

In preferred embodiments the N-containing monocyclic heterocycloalkyl is selected from the group consisting of

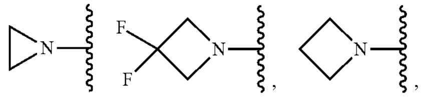
,
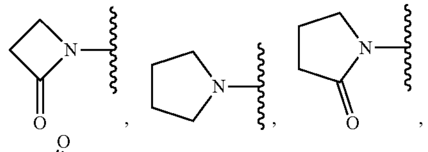
,
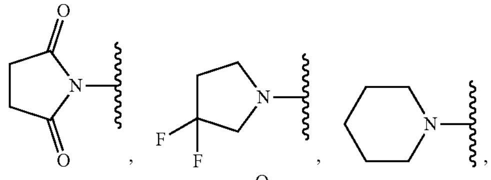
,
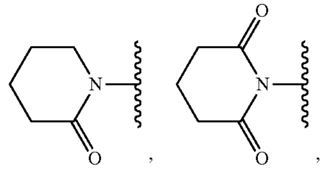
,
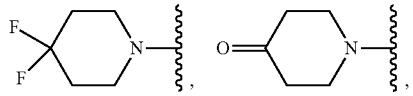
, and
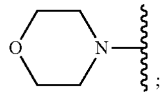
;

In some embodiments G is $CR^6$.

In some embodiments Y is $CR^6$.

In some embodiments Z is $CR^6$.

In some embodiments G is N.

In some embodiments Y is N.

In some embodiments Z is N.

In some embodiments G is absent and the adjacent atoms are joined together to form a 5 membered ring.

In some embodiments Y is absent and the adjacent atoms are joined together to form a 5 membered ring.

In some embodiments Z is absent and the adjacent atoms are joined together to form a 5 membered ring.

In some embodiments Y is N.

In some embodiments Z is N.

In some embodiments R is hydrogen.

In some embodiments R is $C_{1-6}$ alkyl.

In some embodiments $R^1$ is hydrogen.

In some embodiments $R^1$ is halogen.

In some embodiments $R^1$ is optionally substituted $C_{1-6}$ haloalkyl.

In some embodiments $R^1$ is optionally substituted $C_{1-6}$ alkenyl.

In some embodiments $R^1$ is $CO_2R^7$.

In some embodiments $R^1$ is $CONHR^8$.

In some embodiments $R^1$ is $NHR^9$.

In some embodiments $R^1$ is $NR^9R^{10}$.

In some embodiments $R^1$ is $OR^{10}$.

In some embodiments $R^1$ is cyano.

In some embodiments $R^1$ is $N_3$.

In some embodiments $R^1$ is $SO_2R^{11}$.

In some embodiments $R^1$ is optionally substituted phenyl.

In some embodiments $R^1$ is optionally substituted heteroaryl.

In some embodiments $R^1$ is N-containing monocyclic heterocycloalkyl.

In some embodiments $R^1$ is selected from the group consisting of

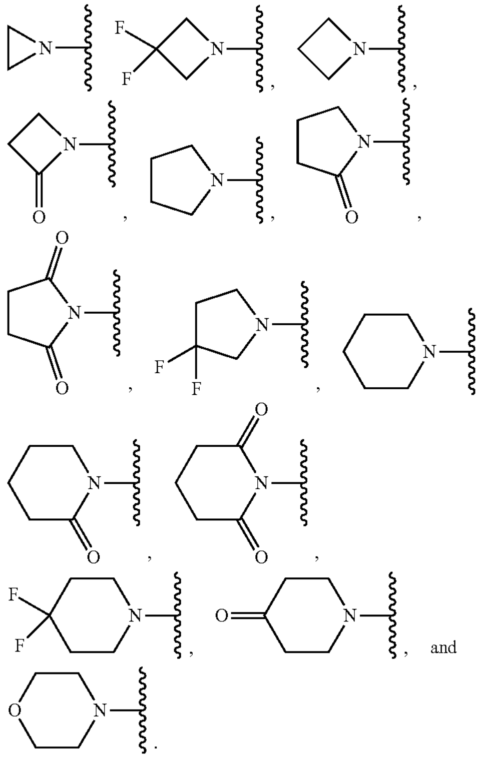

and

In some embodiments $R^2$ is hydrogen.

In some embodiments $R^2$ is halogen.

In some embodiments R is optionally substituted $C_{1-6}$ haloalkyl.

In some embodiments $R^2$ is optionally substituted $C_{1-6}$ alkenyl.

In some embodiments $R^2$ is $CO_2R^7$.

In some embodiments $R^2$ is $CONHR^8$.

In some embodiments $R^2$ is $NHR^9$.

In some embodiments $R^2$ is $NR^9R^{10}$.

In some embodiments $R^2$ is $OR^{10}$.

In some embodiments $R^2$ is cyano.

In some embodiments $R^2$ is $N_3$.

In some embodiments $R^2$ is $SO_2R^{11}$.

In some embodiments $R^2$ is optionally substituted phenyl.

In some embodiments $R^2$ is optionally substituted heteroaryl.

In some embodiments $R^2$ is N-containing monocyclic heterocycloalkyl

In some embodiments $R^2$ is selected from the group consisting of

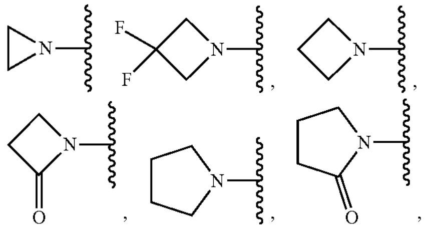

-continued

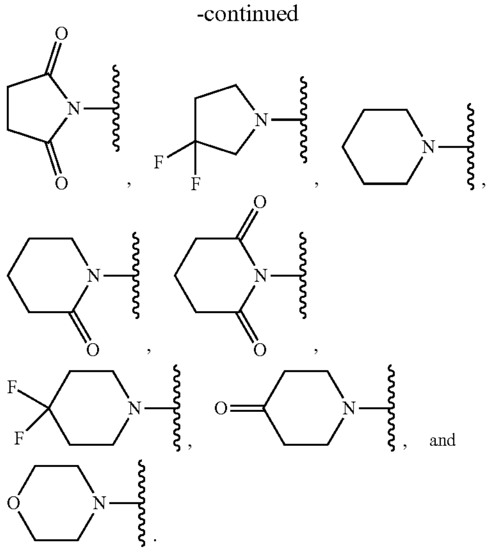

and

In some embodiments $R^3$ is hydrogen.

In some embodiments $R^3$ is halogen.

In some embodiments $R^3$ is optionally substituted $C_{1-6}$ haloalkyl.

In some embodiments $R^3$ is optionally substituted $C_{1-6}$ alkenyl.

In some embodiments $R^3$ is $CO_2R^7$.

In some embodiments $R^3$ is $CONHR^8$.

In some embodiments $R^3$ is $NHR^9$.

In some embodiments $R^3$ is $NR^9R^{10}$.

In some embodiments $R^3$ is $OR^{10}$.

In some embodiments $R^3$ is cyano.

In some embodiments $R^3$ is $N_3$.

In some embodiments $R^3$ is $SO_2R^{11}$.

In some embodiments $R^3$ is optionally substituted phenyl.

In some embodiments $R^3$ is optionally substituted heteroaryl.

In some embodiments $R^3$ is N-containing monocyclic heterocycloalkyl.

In some embodiments $R^3$ is selected from the group consisting of

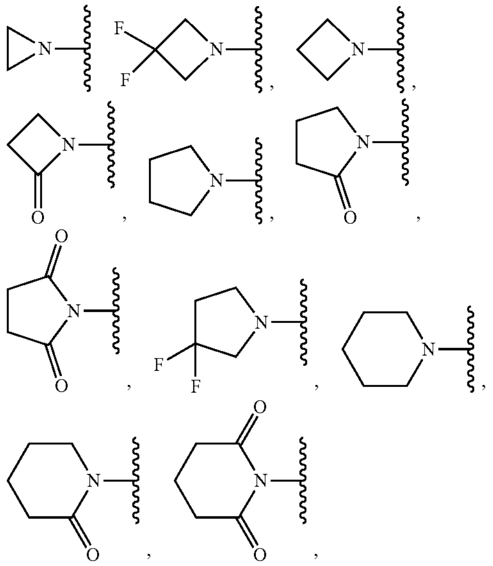

-continued

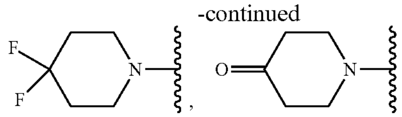

, , and

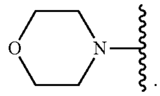

.

In some embodiments $R^4$ is hydrogen.

In some embodiments $R^4$ is halogen.

In some embodiments $R^4$ is optionally substituted $C_{1-6}$ haloalkyl.

In some embodiments $R^4$ is optionally substituted $C_{1-6}$ alkenyl.

In some embodiments $R^4$ is $CO_2R^7$.

In some embodiments $R^4$ is $CONHR^8$.

In some embodiments $R^4$ is $NHR^9$.

In some embodiments $R^4$ is $NR^9R^{10}$.

In some embodiments $R^4$ is $OR^{10}$.

In some embodiments $R^4$ is cyano.

In some embodiments $R^4$ is $N_3$.

In some embodiments $R^4$ is $SO_2R^{11}$.

In some embodiments $R^4$ is optionally substituted phenyl.

In some embodiments $R^4$ is optionally substituted heteroaryl.

In some embodiments $R^4$ is N-containing monocyclic heterocycloalkyl.

In some embodiments $R^4$ is selected from the group consisting of

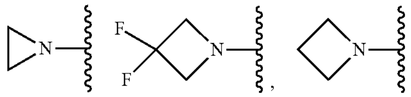

, ,

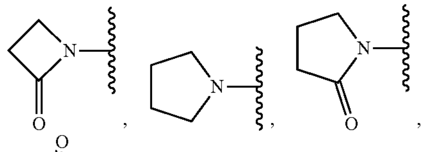

, , ,

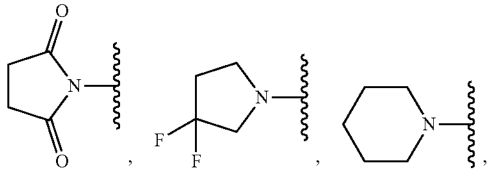

, , ,

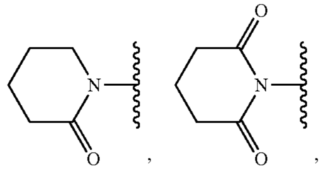

, ,

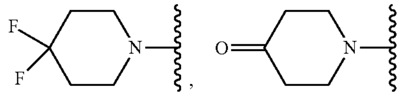

, , and

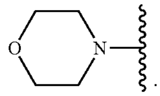

.

In some embodiments R and $R^4$ are taken together to with the atoms to which they are bound to form a ring having 5 members.

In some embodiments R and $R^4$ are taken together to with the atoms to which they are bound to form a ring having 5 members that contains an oxygen.

In some embodiments R and $R^4$ are taken together to with the atoms to which they are bound to form a ring having 5 members that contains a C═O.

In some embodiments R and $R^4$ are taken together to with the atoms to which they are bound to form a ring having 5 members that contains an $SO_2$.

In some embodiments R and $R^4$ are taken together to with the atoms to which they are bound to form a ring having 6 members.

In some embodiments R and $R^4$ are taken together to with the atoms to which they are bound to form a ring having 6 members that contains an oxygen.

In some embodiments R and $R^4$ are taken together to with the atoms to which they are bound to form a ring having 6 members that contains a C═O.

In some embodiments R and $R^4$ are taken together to with the atoms to which they are bound to form a ring having 6 members that contains an $SO_2$.

In some embodiments R and $R^4$ are taken together to with the atoms to which they are bound to form a ring having 7 members.

In some embodiments R and $R^4$ are taken together to with the atoms to which they are bound to form a ring having 7 members that contains an oxygen.

In some embodiments R and $R^4$ are taken together to with the atoms to which they are bound to form a ring having 7 members that contains a C═O.

In some embodiments R and $R^4$ are taken together to with the atoms to which they are bound to form a ring having 7 members that contains an $SO_2$.

In some embodiments R and $R^4$ are taken together to with the atoms to which they are bound to form a ring having 8 members;

In some embodiments R and $R^4$ are taken together to with the atoms to which they are bound to form a ring having 8 members that contains an oxygen.

In some embodiments R and $R^4$ are taken together to with the atoms to which they are bound to form a ring having 8 members that contains a C═O.

In some embodiments R and $R^4$ are taken together to with the atoms to which they are bound to form a ring having 8 members that contains an $SO_2$.

In some embodiments $R^5$ is hydrogen.

In some embodiments $R^5$ is halogen.

In some embodiments $R^5$ is optionally substituted $C_{1-6}$ haloalkyl.

In some embodiments $R^5$ is optionally substituted $C_{1-6}$ alkenyl.

In some embodiments $R^5$ is $CO_2R^7$.

In some embodiments $R^5$ is $CONHR^8$.

In some embodiments $R^5$ is $NHR^9$.

In some embodiments $R^5$ is $NR^9R^{10}$.

In some embodiments $R^5$ is $OR^{10}$.

In some embodiments $R^5$ is cyano.

In some embodiments $R^5$ is $N_3$.

In some embodiments $R^5$ is $SO_2R^{11}$.

In some embodiments $R^5$ is optionally substituted phenyl.

In some embodiments $R^5$ is optionally substituted heteroaryl.

In some embodiments $R^5$ is N-containing monocyclic heterocycloalkyl.

In some embodiments $R^5$ is selected from the group consisting of

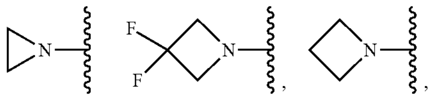

, ,

-continued

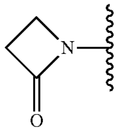, 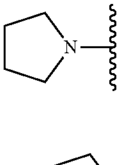, 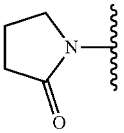,

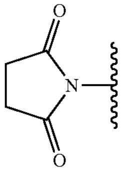, 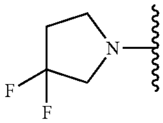, 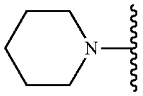,

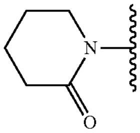, 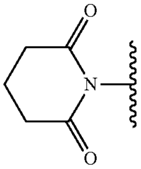,

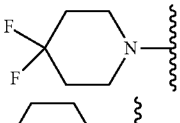, 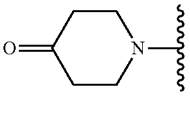, and

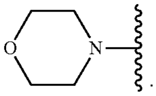.

In some embodiments $R^6$ is hydrogen.

In some embodiments $R^6$ is halogen.

In some embodiments $R^6$ is optionally substituted $C_{1-6}$ haloalkyl.

In some embodiments $R^6$ is optionally substituted $C_{1-6}$ alkenyl.

In some embodiments $R^6$ is $CO_2R^7$.

In some embodiments $R^6$ is $CONHR^8$.

In some embodiments $R^6$ is $NHR^9$.

In some embodiments $R^6$ is $NR^9R^{10}$.

In some embodiments $R^6$ is $OR^{10}$.

In some embodiments $R^6$ is cyano.

In some embodiments $R^6$ is $N_3$.

In some embodiments $R^6$ is $SO_2R^{11}$.

In some embodiments $R^6$ is optionally substituted phenyl.

In some embodiments $R^6$ is optionally substituted heteroaryl.

In some embodiments $R^6$ is N-containing monocyclic heterocycloalkyl.

In some embodiments $R^6$ is selected from the group consisting of

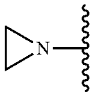 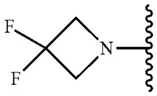, 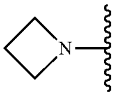,

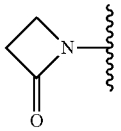, 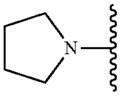, 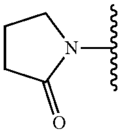,

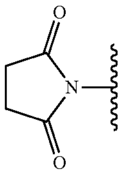, 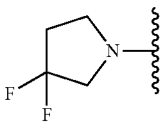, 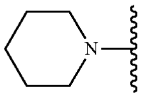,

-continued

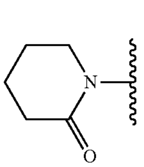, 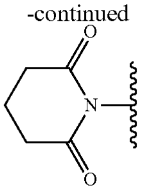,

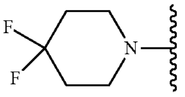, 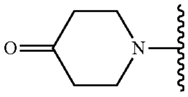, and

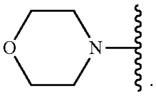.

In some embodiments R and $R^6$ are taken together to with the atoms to which they are bound to form a ring having 5 members.

In some embodiments R and $R^6$ are taken together to with the atoms to which they are bound to form a ring having 6 members.

In some embodiments R and $R^6$ are taken together to with the atoms to which they are bound to form a ring having 7 members.

In some embodiments R and $R^6$ are taken together to with the atoms to which they are bound to form a ring having 8 members.

In some embodiments $R^1$ and $R^6$ are taken together to with the atoms to which they are bound to form an optionally substituted ring having 5 members.

In some embodiments $R^1$ and $R^6$ are taken together to with the atoms to which they are bound to form an optionally substituted ring having 6 member.

In some embodiments $R^1$ and $R^6$ are taken together to with the atoms to which they are bound to form an optionally substituted ring having 7 members.

In some embodiments $R^2$ and $R^6$ are taken together to with the atoms to which they are bound to form an optionally substituted ring having 5 members.

In some embodiments $R^2$ and $R^6$ are taken together to with the atoms to which they are bound to form an optionally substituted ring having 6 members.

In some embodiments $R^2$ and $R^6$ are taken together to with the atoms to which they are bound to form an optionally substituted ring having 7 members.

In some embodiments $R^2$ and $R^6$ are taken together with the atom to which they are bound to form an optionally substituted aromatic ring having 5 ring atoms, optionally containing an oxygen.

In some embodiments $R^2$ and $R^6$ are taken together with the atom to which they are bound to form an optionally substituted aromatic ring having 5 ring atoms, optionally containing a sulfur.

In some embodiments $R^2$ and $R^6$ are taken together with the atom to which they are bound to form an optionally substituted aromatic ring having 5 ring atoms, optionally containing a nitrogen.

In some embodiments $R^2$ and $R^6$ are taken together with the atom to which they are bound to form an optionally substituted aromatic ring having 5 ring atoms, optionally containing an NH.

In some embodiments $R^2$ and $R^6$ are taken together with the atom to which they are bound to form an optionally substituted aromatic ring having 6 ring atoms, optionally containing an oxygen.

In some embodiments $R^2$ and $R^6$ are taken together with the atom to which they are bound to form an optionally substituted aromatic ring having 6 ring atoms, optionally containing a sulfur.

In some embodiments $R^2$ and $R^6$ are taken together with the atom to which they are bound to form an optionally substituted aromatic ring having 6 ring atoms, optionally containing a nitrogen.

In some embodiments $R^2$ and $R^6$ are taken together with the atom to which they are bound to form an optionally substituted aromatic ring having 6 ring atoms, optionally containing an NH.

In some embodiments $R^4$ and $R^5$ are taken together with the atom to which they are bound to form an optionally substituted ring having 5 ring atoms optionally containing a moiety selected from oxygen, sulfur, nitrogen, and NH.

In some embodiments $R^4$ and $R^5$ are taken together with the atom to which they are bound to form an optionally substituted ring having 6 ring atoms optionally containing a moiety selected from oxygen, sulfur, nitrogen, and NH.

In some embodiments $R^4$ and $R^5$ are taken together with the atom to which they are bound to form an optionally substituted ring having 7 ring atoms optionally containing a moiety selected from oxygen, sulfur, nitrogen, and NH.

In some embodiments $R^4$ and $R^5$ are taken together with the atom to which they are bound to form an optionally substituted aromatic ring having 5 ring atoms optionally containing zero to three moieties selected from oxygen, sulfur, nitrogen, and NH.

In some embodiments $R^4$ and $R^5$ are taken together with the atom to which they are bound to form an optionally substituted aromatic ring having 6 ring atoms optionally containing zero to three moieties selected from oxygen, sulfur, nitrogen, and NH.

In some embodiments $R^7$ is hydrogen.

In some embodiments $R^7$ is optionally substituted $C_{1-4}$ alkyl.

In some embodiments $R^7$ is optionally substituted $C_3$-$C_7$ cycloalkyl.

In some embodiments $R^7$ is optionally substituted phenyl.

In some embodiments $R^8$ is hydrogen.

In some embodiments $R^8$ is optionally substituted $C_{1-4}$ alkyl.

In some embodiments $R^8$ is optionally substituted $C_3$-$C_7$ cycloalkyl.

In some embodiments $R^8$ is optionally substituted phenyl.

In some embodiments $R^9$ is hydrogen.

In some embodiments $R^9$ is optionally substituted $C_{1-4}$ alkyl.

In some embodiments $R^9$ is optionally substituted $C_3$-$C_7$ cycloalkyl.

In some embodiments $R^9$ is optionally substituted phenyl.

In some embodiments $R^9$ is optionally substituted heteroaryl.

In some embodiments $R^9$ is $COR^{10}$.

In some embodiments $R^9$ is $SO_2R^{10}$.

In some embodiments $R^{10}$ is hydrogen.

In some embodiments $R^{10}$ is optionally substituted $C_{1-4}$ alkyl.

In some embodiments $R^{10}$ is optionally substituted $C_3$-$C_7$ cycloalkyl.

In some embodiments $R^{10}$ is and optionally substituted phenyl.

In some embodiments $R^9$ and $R^{10}$ units are taken together with the atoms to which they are bound to form a ring having 5 ring atoms.

In some embodiments $R^9$ and $R^{10}$ units are taken together with the atoms to which they are bound to form a ring having 6 ring atoms.

In some embodiments $R^9$ and $R^{10}$ units are taken together with the atoms to which they are bound to form a ring having 7 ring atoms.

In some embodiments $R^9$ and $R^{10}$ units are taken together with the atoms to which they are bound to form a ring having 8 ring atoms.

In some embodiments two $R^{10}$ units are taken together with the atoms to which they are bound to form a ring having 5 ring atoms.

In some embodiments two $R^{10}$ units are taken together with the atoms to which they are bound to form a ring having 6 ring atoms.

In some embodiments two $R^{10}$ units are taken together with the atoms to which they are bound to form a ring having 7 ring atoms.

In some embodiments two $R^{10}$ units are taken together with the atoms to which they are bound to form a ring having 8 ring atoms.

In some embodiments $R^{11}$ is hydrogen.

In some embodiments $R^{11}$ is optionally substituted $C_{1-4}$ alkyl.

In some embodiments $R^{11}$ is optionally substituted $C_3$-$C_7$ cycloalkyl.

In some embodiments $R^{11}$ is optionally substituted phenyl.

In some embodiments n is 1.

In some embodiments n is 2.

In some embodiments n is 3.

In some embodiments $R^{12}$ is hydrogen.

In some embodiments $R^{12}$ is halogen.

In some embodiments $R^{12}$ is optionally substituted $C_{1-6}$ haloalkyl.

In some embodiments $R^{12}$ is optionally substituted $C_{1-6}$ alkenyl.

In some embodiments $R^{12}$ is $CO_2R^7$.

In some embodiments $R^{12}$ is $CONHR^8$.

In some embodiments $R^{12}$ is $NHCOR^9$.

In some embodiments $R^{12}$ is $OR^{10}$.

In some embodiments $R^{12}$ is cyano.

In some embodiments $R^{12}$ is $N_3$.

In some embodiments $R^{12}$ is $SO_2R^{11}$.

In some embodiments $R^{12}$ is optionally substituted phenyl.

In some embodiments $R^{12}$ is optionally substituted heteroaryl.

In some embodiments $R^{12}$ is N-containing monocyclic heterocycloalkyl.

In some embodiments $R^{12}$ is selected from the group consisting of

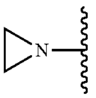

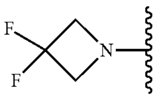,

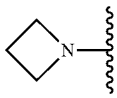,

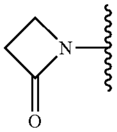,

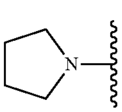,

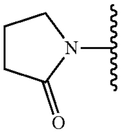,

-continued

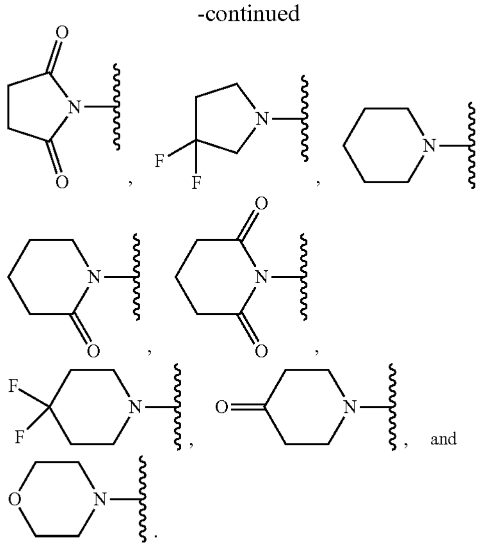

In some embodiments $R^{13}$ is hydrogen.

In some embodiments $R^{13}$ is halogen.

In some embodiments $R^{13}$ is optionally substituted $C_{1-6}$ haloalkyl.

In some embodiments $R^{13}$ is optionally substituted $C_{1-6}$ alkenyl.

In some embodiments $R^{13}$ is $CO_2R^7$.

In some embodiments $R^{13}$ is $CONHR^8$.

In some embodiments $R^{13}$ is $NHCOR^9$.

In some embodiments $R^{13}$ is $OR^{10}$.

In some embodiments $R^{13}$ is cyano.

In some embodiments $R^{13}$ is $N_3$.

In some embodiments $R^{13}$ is $SO_2R^{11}$.

In some embodiments $R^{13}$ is optionally substituted phenyl.

In some embodiments $R^{13}$ is optionally substituted heteroaryl.

In some embodiments $R^{13}$ is N-containing monocyclic heterocycloalkyl.

In some embodiments $R^{13}$ is selected from the group consisting of

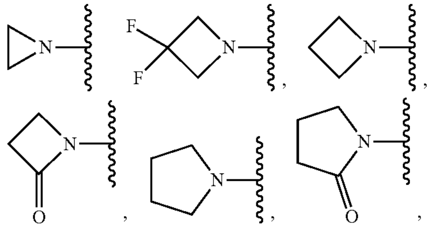

-continued

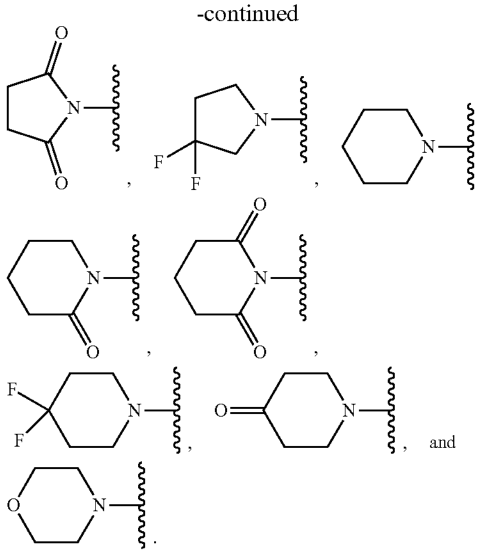

In some embodiments M is O.

In some embodiments M is S.

In some embodiments M is NH.

In some embodiments m is 1.

In some embodiments m is 2.

In some embodiments m is 3.

In some embodiments p is 0.

In some embodiments p is 1.

In some embodiments p is 2.

In some embodiments p is 3.

In some embodiments r is 0.

In some embodiments r is 1.

In some embodiments r is 2.

In some embodiments r is 3.

In some embodiments Q is $CH_2$.

In some embodiments Q is O.

In some embodiments Q is C═O.

In some embodiments Q is $SO_2$.

Exemplary embodiments include compounds having the formula (II) or a pharmaceutically acceptable salt form thereof:

(II)

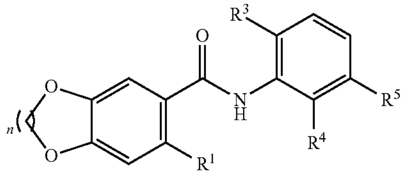

wherein non-limiting examples of n, $R^1$, $R^3$, $R^4$, and $R^5$ defined herein below in Table 1.

TABLE 1

| Table | n | $R^1$ | $R^3$ | $R^4$ | $R^5$ | Entry | n | $R^1$ | $R^3$ | $R^4$ | $R^5$ |
|---|---|---|---|---|---|---|---|---|---|---|---|
| 1 | 1 | Br | H | 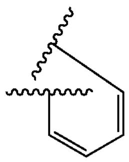 [SMILES: */C=C\C=C/*] | | 24 | 1 | Br | Me | Me | H |

TABLE 1-continued
| Table | n | $R^1$ | $R^3$ | $R^4$ | $R^5$ | Entry | n | $R^1$ | $R^3$ | $R^4$ | $R^5$ |
|---|---|---|---|---|---|---|---|---|---|---|---|
| 2 | 1 | H | H | 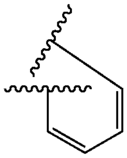 [SMILES: */C=C\C=C/*] | | 25 | 1 | Br | H | 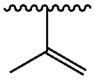 | H |
| 3 | 1 | Br | H | 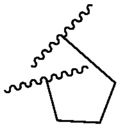 [SMILES: *CCC*] | | 26 | 1 | Br | H | Me | F |
| 4 | 1 | Br | H | 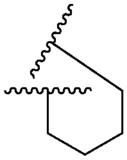 [SMILES: *CCCC*] | | 27 | 1 | Br | H | Cl | H |
| 5 | 1 | Br | H | 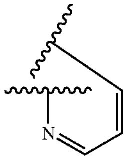 [SMILES: */C=C\C=N/*] | | 28 | 1 | Br | H | H | Cl |
| 6 | 1 | Br | H | H | H | 29 | 1 | Br | H | F | CN |
| 7 | 1 | Br | H | 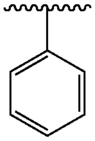 | H | 30 | 1 | Br | H | F | H |
| 8 | 1 | Br | H | 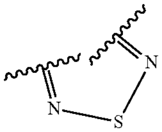 [SMILES: *=NSN=*] | | 31 | 1 | Br | H | 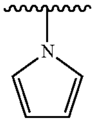 [SMILES: *n1cccc1] | H |
| 9 | 1 | Br | H | Br | Me | 32 | 1 | Br | H | 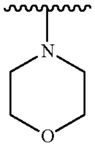 | H |
| 10 | 1 | Br | H | Me | Br | 33 | 1 | Br | H | Me | H |
| 11 | 1 | Br | H | Cl | Cl | 34 | 2 | H | H | 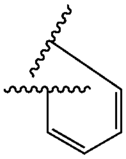 [SMILES: */C=C\C=C/*] | |
| 12 | 1 | Br | H | Me | Me | 35 | 3 | H | H | 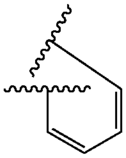 [SMILES: */C=C\C=C/*] | |

TABLE 1-continued
| Table | n | $R^1$ | $R^3$ | $R^4$ | $R^5$ | Entry | n | $R^1$ | $R^3$ | $R^4$ | $R^5$ |
|---|---|---|---|---|---|---|---|---|---|---|---|
| 13 | 1 | Br | H | Me | OBn | 36 | 1 | 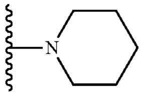 [SMILES: *N1CCCCC1] | H | 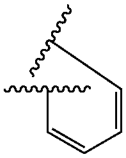 [SMILES: */C=C\C=C/*] | |
| 14 | 1 | OH | H | 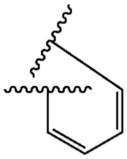 [SMILES: */C=C\C=C/*] | | 37 | 1 | 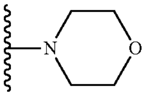 | H | 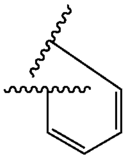 [SMILES: */C=C\C=C/*] | |
| 15 | 1 | OMe | H | 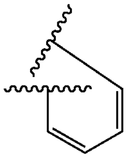 [SMILES: */C=C\C=C/*] | | 38 | 1 | 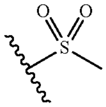 [SMILES: *S(C)(=O)=O] | H | 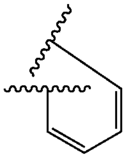 [SMILES: */C=C\C=C/*] | |
| 16 | 1 | 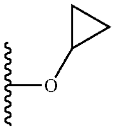 [SMILES: *OC1CC1] | H | 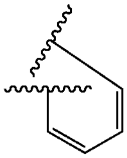 [SMILES: */C=C\C=C/*] | | 39 | 1 | 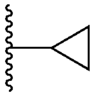 | H | 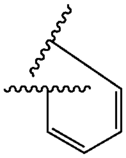 [SMILES: */C=C\C=C/*] | |
| 17 | 1 | $NH_2$ | H | 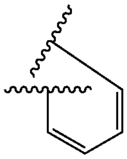 [SMILES: */C=C\C=C/*] | | 40 | 1 | 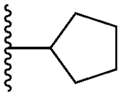 [SMILES: *C1CCCC1] | H | 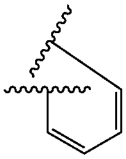 [SMILES: */C=C\C=C/*] | |
| 18 | 1 | $NMe_2$ | H | 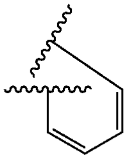 [SMILES: */C=C\C=C/*] | | 41 | 1 | 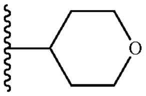 | H | 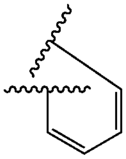 [SMILES: */C=C\C=C/*] | |
| 19 | 1 | 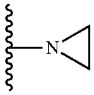 | H | 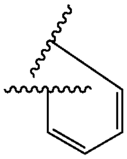 [SMILES: */C=C\C=C/*] | | 42 | 1 | 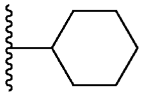 | H | 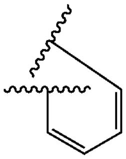 [SMILES: */C=C\C=C/*] | |
| 20 | 1 | 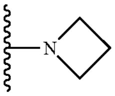 [SMILES: *N1CCC1] | H | 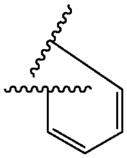 | | 43 | 1 | 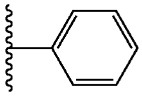 [SMILES: *c1ccccc1] | H | 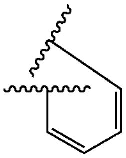 | |
| 21 | 1 | 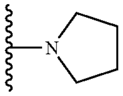 | H | 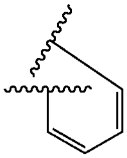 | | 44 | 1 | 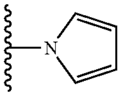 | H | 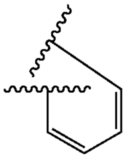 [SMILES: */C=C\C=C/*] | |

TABLE 1-continued

| Table | n | $R^1$ | $R^3$ | $R^4$ | $R^5$ | Entry | n | $R^1$ | $R^3$ | $R^4$ | $R^5$ |
|---|---|---|---|---|---|---|---|---|---|---|---|
| 22 | 1 | $CF_3$ | H | 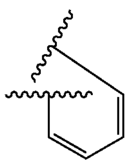 [SMILES: */C=C\C=C/*] | | 45 | 1 | $CHF_2$ | H | 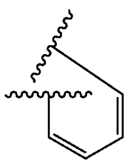 | |
| 23 | 1 | CN | H | 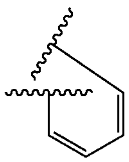 [SMILES: */C=C\C=C/*] | | 46 | 1 | COOEt | H | 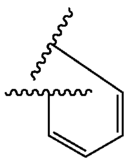 [SMILES: */C=C\C=C/*] | |

Exemplary embodiments include compounds having the formula (V) or a pharmaceutically acceptable salt form thereof:

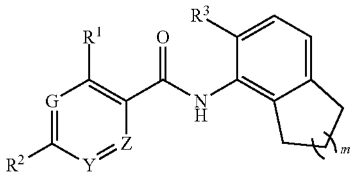

(V)

wherein non-limiting examples of m, $R^1$, $R^2$, $R^3$, G, Y, and Z defined herein below in Table 2.

TABLE 2

| Entry | m | $R^1$ | $R^2$ | $R^3$ | G | Y | Z |
|---|---|---|---|---|---|---|---|
| 1 | 1 | Br | F | H | CH | CF | CH |
| 2 | 1 | OH | F | H | CH | CH | CH |
| 3 | 1 | OMe | F | H | CH | CH | CH |
| 4 | 1 | 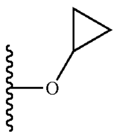 [SMILES: *OC1CC1] | F | H | CH | CH | CH |
| 5 | 1 | $NH_2$ | F | H | CH | CH | CH |
| 6 | 1 | $NMe_2$ | F | H | CH | CH | CH |
| 7 | 1 | 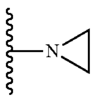 [SMILES: *N1CC1] | F | H | CH | CH | CH |
| 8 | 1 | 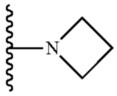 [SMILES: *N1CCC1] | F | H | CH | CH | CH |
| 9 | 1 | 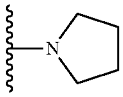 [SMILES: *N1CCCC1] | F | H | CH | CH | CH |

TABLE 2-continued

| Entry | m | $R^1$ | $R^2$ | $R^3$ | G | Y | Z |
|---|---|---|---|---|---|---|---|
| 10 | 1 | 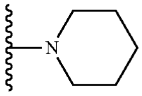 | F | H | CH | CH | CH |
| 11 | 1 | 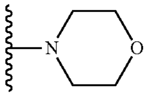 | F | H | CH | CH | CH |
| 12 | 1 | CN | F | H | CH | CH | CH |
| 13 | 1 | $CH_2F$ | F | H | CH | CH | CH |
| 14 | 1 | $CHF_2$ | F | H | CH | CH | CH |
| 15 | 1 | 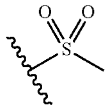 [SMILES: *S(C)(=O)=O] | F | H | CH | CH | CH |
| 16 | 1 | 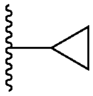 [SMILES: *C1CC1] | F | H | CH | CH | CH |
| 17 | 1 | 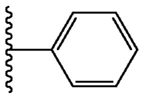 [SMILES: *c1ccccc1] | F | H | CH | CH | CH |
| 18 | 2 | Br | F | H | CH | CF | CH |
| 19 | 2 | OH | F | H | CH | CH | CH |
| 20 | 2 | OMe | F | H | CH | CH | CH |
| 21 | 2 | 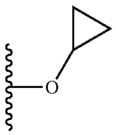 [SMILES: *OC1CC1] | F | H | CH | CH | CH |
| 22 | 2 | NH2 | F | H | CH | CH | CH |
| 23 | 2 | NMe2 | F | H | CH | CH | CH |
| 24 | 2 | 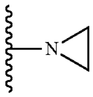 [SMILES: *N1CC1] | F | H | CH | CH | CH |

TABLE 2-continued

| Entry | m | $R^1$ | $R^2$ | $R^3$ | G | Y | Z |
|---|---|---|---|---|---|---|---|
| 25 | 2 | 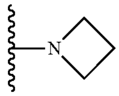 [SMILES: *N1CCC1] | F | H | CH | CH | CH |
| 26 | 2 | 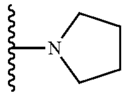 [SMILES: *N1CCCC1] | F | H | CH | CH | CH |
| 27 | 2 | 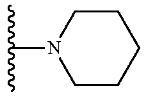 [SMILES: *N1CCCCC1] | F | H | CH | CH | CH |
| 28 | 2 | 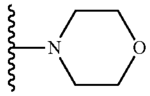 [SMILES: *N1CCOCC1] | F | H | CH | CH | CH |
| 29 | 2 | CN | F | H | CH | CH | CH |
| 30 | 2 | $CH_2F$ | F | H | CH | CH | CH |
| 31 | 2 | CHF2 | F | H | CH | CH | CH |
| 32 | 2 | 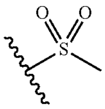 [SMILES: *S(C)(=O)=O] | F | H | CH | CH | CH |
| 33 | 2 | 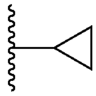 [SMILES: *C1CC1] | F | H | CH | CH | CH |
| 34 | 2 | 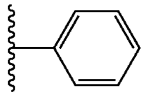 [SMILES: *c1ccccc1] | F | H | CH | CH | CH |

Exemplary embodiments include compounds having the formula (VI) or a pharmaceutically acceptable salt form thereof:

(VI)

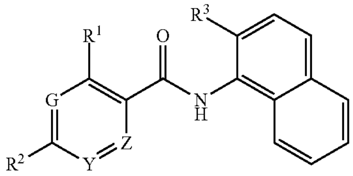

wherein non-limiting examples of $R^1$, $R^2$, $R^3$, G, Y, and Z defined herein below in Table 3.

TABLE 3

| Entry | $R^1$ | $R^2$ | $R^3$ | G | Y | Z |
|---|---|---|---|---|---|---|
| 1 | Br | OMe | H | CH | CH | CH |
| 2 | Br | H | H | CH | CH | CH |
| 3 | Br | OMe | H | CH | C-OMe | CH |
| 4 | Br | H | H | CH | C-OMe | CH |
| 5 | Cl | Cl | H | CH | CH | CH |
| 6 | Br | Cl | H | CH | CH | CH |
| 7 | Me | Cl | H | CH | CH | CH |
| 8 | F | Cl | H | CH | CH | CH |
| 9 | F | Cl | H | CH | CF | CH |

TABLE 3-continued

| Entry | $R^1$ | $R^2$ | $R^3$ | G | Y | Z |
|---|---|---|---|---|---|---|
| 10 | Br | F | H | CH | CF | CH |
| 11 | Br | H | H | CH | CF | CH |
| 12 | Br | F | H | CH | CH | CH |
| 13 | Cl | H | H | C-Cl | CH | CH |
| 14 | Cl | Br | H | CH | CH | CH |
| 15 | Cl | H | H | N | CH | N |
| 16 | Cl | H | H | N | CH | CH |
| 17 | Cl | H | H | CH | CH | CH |
| 18 | Cl | F | H | CH | CH | CH |
| 19 | F | H | H | CH | C-$NO_2$ | CH |
| 20 | F | F | H | CH | CH | CH |
| 21 | F | F | H | CH | CH | CF |
| 22 | F | F | H | CH | CF | CH |
| 23 | F | $CF_3$ | H | CH | CH | CH |
| 24 | 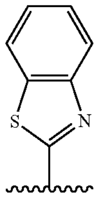 | F | H | CH | CH | CH |
| 25 | $CF_3$ | F | H | CH | CH | CH |

Exemplary embodiments include compounds having the formula (VII) or a pharmaceutically acceptable salt form thereof:

(VII)

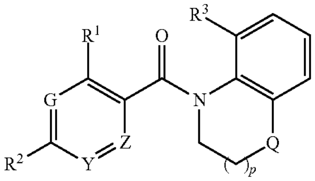

wherein non-limiting examples of p, Q, $R^1$, $R^2$, $R^3$, G, Y, and Z defined herein below in Table 4.

TABLE 4

| Entry | p | Q | $R^1$ | $R^3$ | $R^2$ | Y | G | Z |
|---|---|---|---|---|---|---|---|---|
| 1 | 1 | C=O | Br | H | 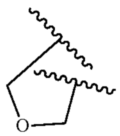 [SMILES: *COC*] | | CH | CH |
| 2 | 0 | $CH_2$ | Br | H | 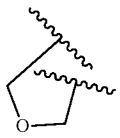 [SMILES: *COC*] | | CH | CH |
| 3 | 0 | $CH_2$ | Br | Cl | 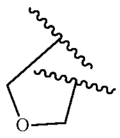 | | CH | CH |

TABLE 4-continued

| Entry | p | Q | $R^1$ | $R^3$ | $R^2$ | Y | G | Z |
|---|---|---|---|---|---|---|---|---|
| 4 | 1 | $CH_2$ | Br | H | 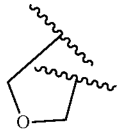 [SMILES: *COC*] | | CH | CH |
| 5 | 0 | $CH_2$ | Br | H | Cl | CH | CH | CH |
| 6 | 0 | $CH_2$ | Br | Me | Cl | CH | CH | CH |
| 7 | 1 | $CH_2$ | Br | H | Cl | CH | CH | CH |
| 8 | 1 | C=O | Br | H | Cl | CH | CH | CH |
| 9 | 0 | $CH_2$ | Br | Cl | Cl | CH | CH | CH |

Exemplary embodiments include compounds having the formula (IX) or a pharmaceutically acceptable salt form thereof:

(IX)

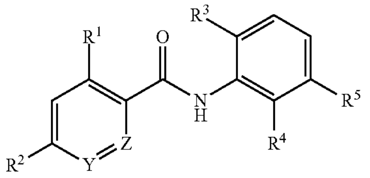

wherein non-limiting examples of $R^1$, $R^2$, $R^3$, $R^4$, $R^5$, Y, and Z defined herein below in Table 5.

TABLE 5

| Entry | $R^1$ | $R^2$ | $R^3$ | $R^4$ | $R^5$ | Y | Z |
|---|---|---|---|---|---|---|---|
| 1 | Br | F | H | Me | Me | CF | CH |
| 2 | CN | F | H | Me | Me | CF | CH |
| 3 | OH | F | H | Me | Me | CF | CH |
| 4 | OMe | F | H | Me | Me | CF | CH |
| 5 | 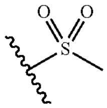 | F | H | Me | Me | CF | CH |
| 6 | 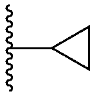 | F | H | Me | Me | CF | CH |
| 7 | 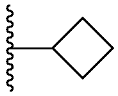 [SMILES: *C1CCC1] | F | H | Me | Me | CF | CH |
| 8 | 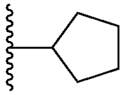 | F | H | Me | Me | CF | CH |
| 9 | 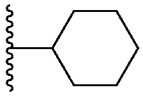 | F | H | Me | Me | CF | CH |
| 10 | 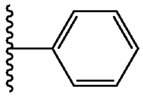 | F | H | Me | Me | CF | CH |

TABLE 5-continued

| Entry | $R^1$ | $R^2$ | $R^3$ | $R^4$ | $R^5$ | Y | Z |
|---|---|---|---|---|---|---|---|
| 11 | 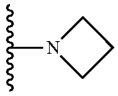 | F | H | Me | Me | CF | CH |
| 12 | 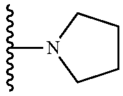 | F | H | Me | Me | CF | CH |
| 13 | 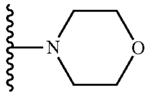 | F | H | Me | Me | CF | CH |
| 14 | Br | F | H | Cl | Cl | CF | CH |
| 15 | CN | F | H | Cl | Cl | CF | CH |
| 16 | OH | F | H | Cl | Cl | CF | CH |
| 17 | OMe | F | H | Cl | Cl | CF | CH |
| 18 | 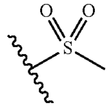 [SMILES: *S(C)(=O)=O] | F | H | Cl | Cl | CF | CH |
| 19 | 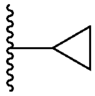 | F | H | Cl | Cl | CF | CH |
| 20 | 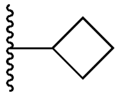 | F | H | Cl | Cl | CF | CH |
| 21 | 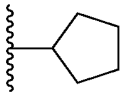 [SMILES: *C1CCCC1] | F | H | Cl | Cl | CF | CH |
| 22 | 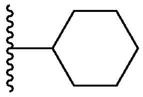 | F | H | Cl | Cl | CF | CH |
| 23 | 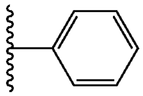 | H | Cl | Cl | CF | CH | |
| 24 | 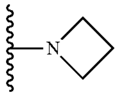 | F | H | Cl | Cl | CF | CH |
| 25 | 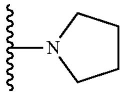 | F | H | Cl | Cl | CF | CH |
| 26 | 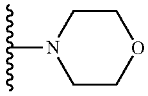 | F | H | Cl | Cl | CF | CH |
| 27 | Me | F | H | Cl | Cl | CF | CH |

Exemplary embodiments include compounds having the formula (X) or a pharmaceutically acceptable salt form thereof:

(X)

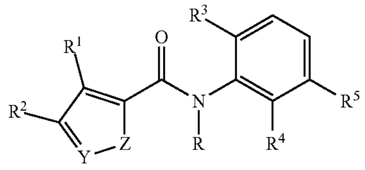

wherein non-limiting examples of R, $R^1$, $R^2$, $R^3$, $R^4$, $R^5$, Y, and Z defined herein below in Table 6.

TABLE 6

| Entry | R | $R^1$ | $R^2$ | Y | Z | $R^3$ | $R^4$ | $R^5$ |
|---|---|---|---|---|---|---|---|---|
| 1 | H | 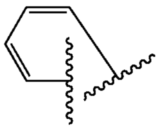 [SMILES: */C=C\C=C/*] | | N-Me | N | H | | 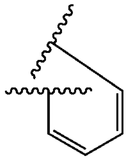 [SMILES: */C=C\C=C/*] |
| 2 | H | Me | 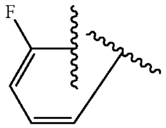 [SMILES: */C=C\C=C(/*)F] | | S | H | | 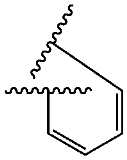 [SMILES: */C=C\C=C/*] |

Exemplary embodiments include compounds having the formula (XII) or a pharmaceutically acceptable salt form thereof:

(XII)

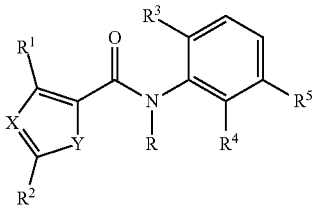

wherein non-limiting examples of R, $R^1$, $R^2$, $R^3$, $R^4$, $R^5$, X, and Z defined herein below in Table 7.

TABLE 7

| Entry | R | $R^1$ | $R^2$ | X | Y | $R^3$ | $R^4$ | $R^5$ |
|---|---|---|---|---|---|---|---|---|
| 1 | H | H | H | N | N-Me | H | | 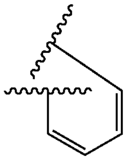 |
| 1 | H | $CF_3$ | H | N | N-Me | H | | 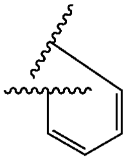 [SMILES: */C=C\C=C/*] |

TABLE 7-continued

| Entry | R | $R^1$ | $R^2$ | X | Y | $R^3$ | $R^4$ | $R^5$ |
|---|---|---|---|---|---|---|---|---|
| 1 | H | CN | H | N | N-Me | H | | 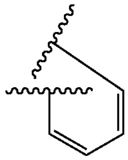 [SMILES: */C=C\C=C/*] |
| 1 | H | 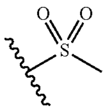 [SMILES: *S(C)(=O)=O] | H | N | N-Me | H | | 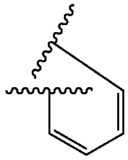 [SMILES: */C=C\C=C/*] |
| 1 | H | COOEt | H | N | N-Me | H | | 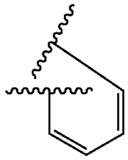 [SMILES: */C=C\C=C/*] |
| 1 | H | Me | H | N | N-Me | H | | 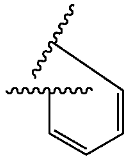 [SMILES: */C=C\C=C/*] |
| 1 | H | 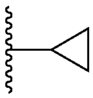 | H | N | N-Me | H | | 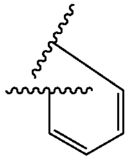 [SMILES: */C=C\C=C/*] |
| 1 | H | 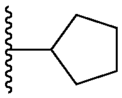 [SMILES: *C1CCCC1] | H | N | N-Me | H | | 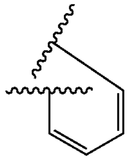 [SMILES: */C=C\C=C/*] |
| 1 | H | 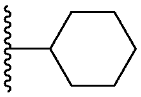 [SMILES: *C1CCCCC1] | H | N | N-Me | H | | 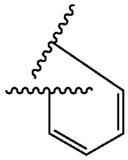 [SMILES: */C=C\C=C/*] |
| 1 | H | 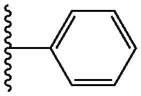 | H | N | N-Me | H | | 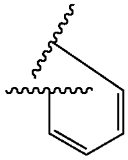 [SMILES: */C=C\C=C/*] |
| 1 | H | 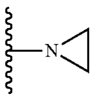 | H | N | N-Me | H | | 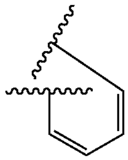 [SMILES: */C=C\C=C/*] |

TABLE 7-continued

| Entry | R | $R^1$ | $R^2$ | X | Y | $R^3$ | $R^4$ | $R^5$ |
|---|---|---|---|---|---|---|---|---|
| 1 | H | 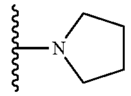 [SMILES: *N1CCCC1] | H | N | N-Me | H | | 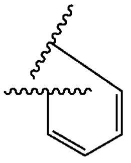 |
| 1 | H | 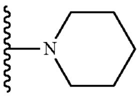 [SMILES: *N1CCCCC1] | H | N | N-Me | H | | 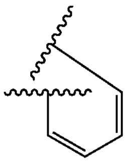 [SMILES: */C=C\C=C/*] |
| 1 | H | 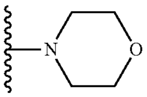 | H | N | N-Me | H | | 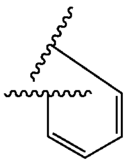 [SMILES: */C=C\C=C/*] |

For the purposes of demonstrating the manner in which the compounds of the present invention are named and referred to herein, the compound having the formula:

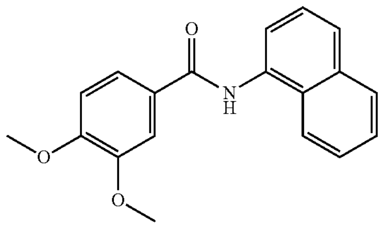 [SMILES: COc1ccc(C(=O)Nc2cccc3ccccc23)cc1OC]

has the chemical name 3,4-dimethoxy-N-(naphthalen-1-yl)benzamide.

For the purposes of demonstrating the manner in which the compounds of the present invention are named and referred to herein, the compound having the formula:

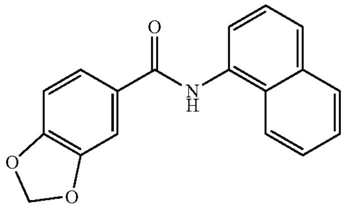 [SMILES: O=C(Nc1cccc2ccccc12)c1ccc2c(c1)OCO2]

has the chemical name N-(naphthalen-1-yl)benzo[d][1,3]dioxole-5-carboxamide.

For the purposes of demonstrating the manner in which the compounds of the present invention are named and referred to herein, the compound having the formula:

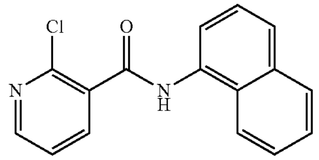 [SMILES: O=C(Nc1cccc2ccccc12)c1cccnc1Cl]

has the chemical name 2-chloro-N-(naphthalen-1-yl)nicotinamide.

Process

The present invention further relates to a process for preparing the novel cyclic GMP-AMP synthase-Stimulator of interferon gene (cGAS-STING) pathway agonists of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high performance liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

General Synthetic Methods

General Synthetic Schemes for Preparation of Compounds.

The reagents used in the preparation of the compounds of this invention can be either commercially obtained or can be prepared by standard procedures described in the literature. In accordance with this invention, compounds in the genus may be produced by one of the following reaction schemes.

The first aspect of the process of the present invention relates to a process for preparing benzamides having the formula (I). Compounds of formula (I) may be prepared according to the process outlined in Schemes 1-4.

Scheme 1

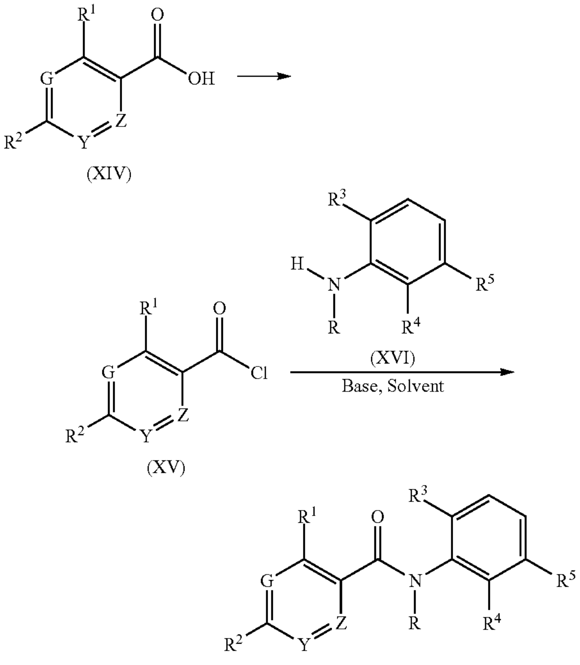

(XIV) (XV) (I)

Accordingly, a suitably substituted compound of the formula (XIV), a known compound or compound prepared by known methods, is reacted with thionyl chloride, optionally in the presence an organic solvent such as methylene chloride, dichloroethane, tetrahydronfuran, 1,4-dioxane, dimethyl formamide, and the like, optionally with heating, optionally with microwave irradiation, to provide a compound of the formula (XV). Alternatively, A compound of the formula (XIV) is reacted with oxalyl chloride, optionally in the presence of dimethyl formamide, optionally in an organic solvent such as methylene chloride, dichloroethane, tetrahydrofuran, 1,4-dioxane, dimethyl formamide, and the like, optionally with heating, optionally with microwave irradiation, to provide a compound of the formula (XV). A compound of the formula (XV) is then reacted with a compound of the formula (XVI), a known compound or compound prepared by known methods, optionally in the presence of a base such as triethylamine, diisopropylethylamine, pyridine, 2,6-lutidine, and the like, optionally in the presence of 4-N,N-dimethylaminopyridine, in an organic solvent such as methylene chloride, dichloroethane, tetrahydrofuran, 1,4-dioxane, dimethyl formamide, and the like, optionally with heating, optionally with microwave irradiation, to provide a compound of the formula (I).

Scheme 2

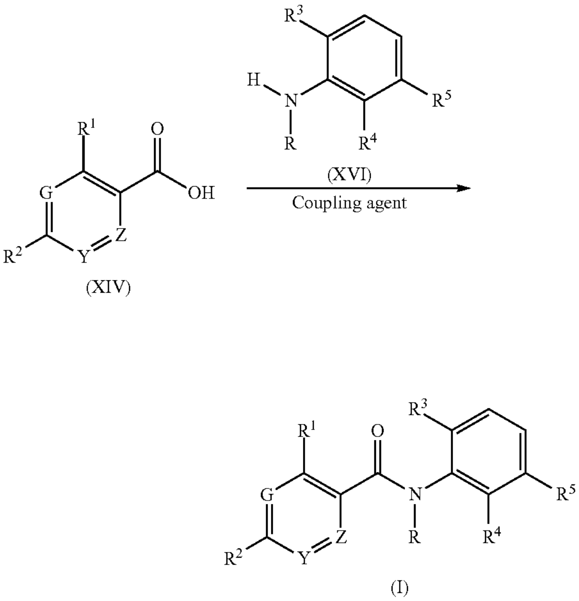

(XIV) (I)

Alternatively, a suitably substituted compound of the formula (XIV), a known compound or compound prepared by known methods, is reacted with a compound of the formula (XVI), a known compound or compound prepared by known methods, in the presence of a coupling agent such as 1-ethyl-3-(3-dimethylaminopropyl) carbodiimide, N,N'-Dicyclohexylcarbodiimide, O-Benzotriazole-N,N,N',N'-tetramethyl-uronium-hexafluoro-phosphate, O-(7-azabenzotriazol-1-yl)-N,N,N',N'-tetramethyluronium hexafluorophosphate, Benzotriazole-1-yl-oxy-tris-(dimethylamino)-phosphonium hexafluorophosphate, benzotriazol-1-yl-oxytripyrrolidinophosphonium hexafluorophosphate, and the like, in an organic solvent such as tetrahydronfuran, 1,4-dioxane, dimethylformamide, methylene chloride, dichloroethane, methanol, ethanol, and the like, optionally in the presence of a base such as triethylamine, diisopropylethylamine, pyridine, 2,6-lutidine, and the like, optionally in the presence of 4-N,N-dimethylaminopyridine, optionally with heating, optionally with microwave irradiation, to provide a compound of the formula (I).

Scheme 3

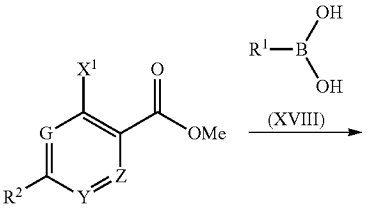

(XVII)

-continued

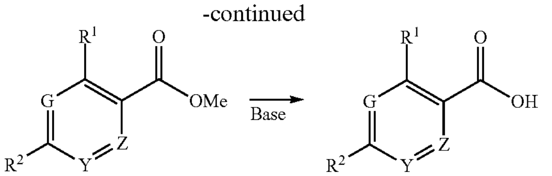

(XIX) (XIV)

A compound of the formula (XVII), a known compound or a compound prepared by known methods wherein $X^1$ is selected from the group consisting of bromine, chlorine, and methanetrifluorosulfonate, is reacted with a compound of the formula (XVIII) a known compound or a compound prepared by known methods, in the presence of a palladium catalyst such as palladium (II) acetate, tetrakis(triphenylphosphine)palladium(0), dichlorobis (triphenyl phosphine)palladium(II), bis(acetonitrile)dichloropalladium(II), tris(dibenzylideneacetone) dipalladium(O), and the like, in the presence of a base such as sodium carbonate, potassium carbonate, lithium carbonate, sodium bicarbonate, potassium bicarbonate, lithium bicarbonate, triethylamine, diisopropylethylamine, pyridine, and the like, optionally in the presence of water, in a solvent such as tetrahydrofuran, 1,4-dioxane, acetonitrile, N,N-dimethyl formamide, N,N-dimethylacetamide, methylene chloride, 1,2-dichloroethane, and the like, optionally with heating, optionally with microwave irradiation to provide a compound of the formula (XIX). A compound of the formula (XIX) is reacted with a base such as sodium hydroxide, lithium hydroxide, potassium hydroxide, sodium carbonate, potassium carbonate, lithium carbonate and the like, in a solvent such as methanol, ethanol, tetrahydrofuran, 1,4-dioxane, acetonitrile, N,N-dimethyl formamide, N,N-dimethylacetamide, optionally in the presence of water, optionally with heating, optionally with microwave irradiation to provide a compound of the formula (XIV).

Scheme 4

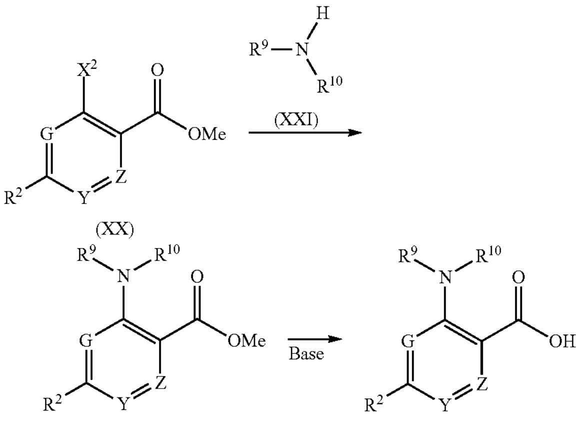

(XX)

(XXII) (XXIII)

A compound of the formula (XX), a known compound or a compound prepared by known methods, is reacted with a compound of the formula (XXI), a known compound or a compound prepared by known methods wherein $X^2$ is selected from the group consisting of chlorine, bromine, iodine, fluorine, and triflouromethane sulfonate, in the presence of a palladium catalyst such as palladium (II) acetate, tetrakis(triphenylphosphine)palladium(0), dichlorobis (triphenylphosphine)palladium(II), bis(acetonitrile)dichloropalladium(II), tris(dibenzylideneacetone)dipalladium(0), or a copper catalyst, such as copper iodide or copper acetate, and the like, in the presence of a base such as sodium tert-butoxide, lithium tert-butoxide, potassium tert-butoxide, pyridine, triethylamine, and the like, optionally in the presence of (±)-2,2'-Bis(diphenylphosphino)-1,1'-binaphthalene, in the presence of a solvent such as toluene, benzene, tetrahydrofuran, 1,4-dioxane, N,N-dimethyl formamide, N,N-dimethylacetamide, methylene chloride, 1,2-dichloroethane, and the like, optionally with heating, optionally with microwave irradiation to provide a compound of the formula (XXII). A compound of the formula (XXII) is reacted with a base such as sodium hydroxide, lithium hydroxide, potassium hydroxide, sodium carbonate, potassium carbonate, lithium carbonate and the like, in a solvent such as methanol, ethanol, tetrahydrofuran, 1,4-dioxane, acetonitrile, N,N-dimethyl formamide, N,N-dimethylacetamide, optionally in the presence of water, optionally with heating, optionally with microwave irradiation to provide a compound of the formula (XXIII).

EXAMPLES

The examples below provide methods for preparing representative compounds of the disclosure. The skilled practitioner will know how to substitute the appropriate reagents, starting materials and purification methods known to those skilled in the art, in order to prepare additional compounds of the present invention.

$^1H$ NMR spectra were recorded on a 300 MHz INOVA VARIAN spectrometer. Chemical shifts values are given in ppm and referred as the internal standard to TMS (tetramethylsilane). The peak patterns are indicated as follows: s, singlet; d, doublet; t, triplet; q, quadruplet; m, multiplet and dd, doublet of doublets. The coupling constants (J) are reported in Hertz (Hz). Mass Spectra were obtained on a 1200 Aligent LC-MS spectrometer (ES-API, Positive). Silica gel column chromatography was performed over silica gel 100-200 mesh, and the eluent was a mixture of ethyl acetate and hexanes, or mixture of methanol and ethyl acetate. All the tested compounds possess a purity of at least 95%. Analytical HPLC (acetonitrile-water buffered with 0.1% formic acid) was run on the Agilent 1100 HPLC instrument, equipped with Agilent, ZORBAX SB-C18 column and UV detection at 210 nm.

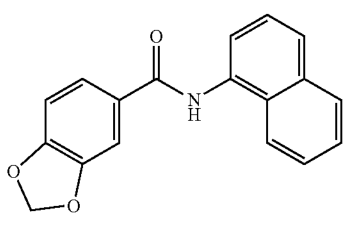 [SMILES: O=C(Nc1cccc2ccccc12)c1ccc2c(c1)OCO2]

Example 1: N-(naphthalen-1-yl)benzo[d][1,3]dioxole-5-carboxamide: Piperonylic acid (0.0829 g, 0.499 mmol), 1-aminonaphthalene (0.080 g, 0.5586 mmol) and (2-(1H-benzotriazol-1-yl)-1,1,3,3-tetramethyluronium hexafluorophosphate) (HBTU, 0.2068 g, 0.5453 mmol) were dissolved in N,N-dimethylformamide (DMF, 1 mL) and treated with N,N-diisopropylethylamine (0.26 mL). The mixture was stirred at 22° C. for 18 hours. Ethyl acetate (20 mL) was added to dilute the mixture and the mixture was washed with HCl (5 mL, 1M, twice), saturated $NaHCO_3$ solution, and saturated brine, subsequently, concentrated under vacuum, and purified using normal phase chromatography (12 g Isco silica column, Ethyl acetate-Hexane, 0~30%) to give a white solid (0.0562 g, 38.65%). $^1H$ NMR (300 MHz, $CDCl_3$): δ 8.05-8.02 (m, 2H), 7.91-7.89 (m, 2H), 7.74 (d, J=7.5 Hz, 1H), 7.55-7.48 (m, 5H), 6.94 (d, J=9 Hz, 1H), 6.09 (s, 2H, $OCH_2O$). Calculated MS for $C_{18}H_{13}NO_3$, 291.09; observed, $(M+H)^+$ 292.3.

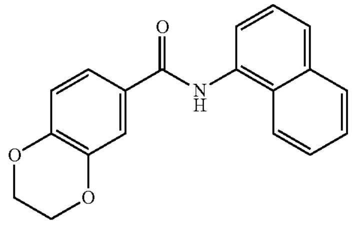 [SMILES: O=C(Nc1cccc2ccccc12)c1ccc2c(c1)OCCO2]

Example 2: N-(naphthalen-1-yl)-2,3-dihydrobenzo[b][1,4]dioxine-6-carboxamide: 1,4-Benzodioxane-6-carboxylic acid (0.0860 g, 0.4773 mmol), 1-aminonaphthalene (0.0752 g, 0.525 mmol) and (2-(1H-benzotriazol-1-yl)-1,1,3,3-tetramethyluronium hexafluorophosphate) (HBTU, 0.1991 g, 0.525 mmol) were dissolved in N,N-dimethylformamide (DMF, 1 mL) and treated with N,N-diisopropylethylamine (0.25 mL). The mixture was stirred at 22° C. for 18 hours. Ethyl acetate (20 mL) was added to dilute the mixture and the mixture was washed with HCl (5 mL, 1M, twice), saturated $NaHCO_3$ solution, and saturated brine, subsequently, concentrated under vacuum, and purified using normal phase chromatography (12 g Isco silica column, Ethyl acetate-Hexane, 0~30%) to give a white solid (0.0737 g, 50.58%). $^1H$ NMR (300 MHz, $CDCl_3$): δ 8.10-8.05 (m, 2H), 7.90-7.89 (m, 2H), 7.73 (d, J=6 Hz, 1H), 7.54-7.52 (m, 5H), 7.00-6.98 (m, 1H), 4.34 (s, 4H, $OCH_2CH_2O$). Calculated MS for $C_{19}H_{15}NO_3$, 305.11; observed, $(M+H)^+$ 306.3.

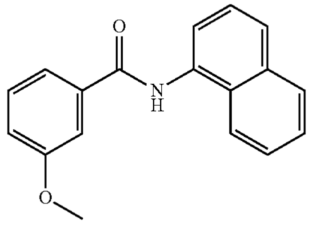 [SMILES: COc1cccc(C(=O)Nc2cccc3ccccc23)c1]

Example 3: 3-methoxy-N-(naphthalen-1-yl)benzamide: 3-Methoxybenzoic acid (0.0796 g, 0.5231 mmol), 1-aminonaphthalene (0.0824 g, 0.5754 mmol) and (2-(1H-benzotriazol-1-yl)-1,1,3,3-tetramethyluronium hexafluorophosphate) (HBTU, 0.2182 g, 0.5754 mmol) were dissolved in N,N-dimethylformamide (DMF, 1 mL) and treated with N,N-diisopropylethylamine (0.27 mL). The mixture was stirred at 22° C. for 18 hours. Ethyl acetate (20 mL) was added to dilute the mixture and the mixture was washed with HCl (5 mL, 1M, twice), saturated $NaHCO_3$ solution, saturated brine, subsequently, concentrated under vacuum, and purified using normal phase chromatography (12 g Isco silica column, Ethyl acetate-Hexane, 0~25%) to give a white solid (0.0861 g, 59.34%). $^1H$ NMR (300 MHz, $CDCl_3$): δ 8.19 (s, 1H), 8.09-8.07 (m, 2H), 7.92-7.91 (m, 2H), 7.76 (d, J=6 Hz, 1H), 7.55-7.45 (m, 6H), 7.15-7.13 (m, 1H), 3.91 (s, 3H, $OCH_3$). Calculated MS for $C_{18}H_{15}NO_2$, 277.11; observed, $(M+H)^+$ 278.4.

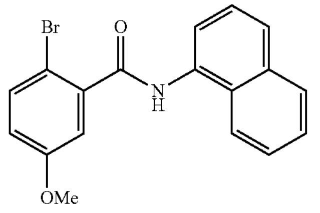 [SMILES: COc1ccc(Br)c(C(=O)Nc2cccc3ccccc23)c1]

Example 4: 2-bromo-6-methoxy-N-(naphthalen-1-yl)benzamide: 2-Bromo-5-methoxybenzoic acid (0.0634 g, 0.2744 mmol), 1-aminonaphthalene (0.0432 g, 0.3018 mmol) and (2-(1H-benzotriazol-1-yl)-1,1,3,3-tetramethyluronium hexafluorophosphate) (HBTU, 0.1145 g, 0.3018 mmol) were dissolved in N,N-dimethylformamide (DMF, 1 mL) and treated with N,N-diisopropylethylamine (0.14 mL). The mixture was stirred at 22° C. for 18 hours. Ethyl acetate (20 mL) was added to dilute the mixture and the mixture was washed with HCl (5 mL, 1M, twice), saturated $NaHCO_3$ solution, saturated brine, subsequently, concentrated under vacuum and purified using normal phase chromatography (12 g Isco silica column, Ethyl acetate-Hexane, 0~25%) to give a white solid (0.0604 g, 61.82%). $^1H$ NMR (300 MHz, $CDCl_3$): δ 8.16-8.14 (m, 2H), 8.03-8.01 (m, 1H), 7.92-7.89 (m, 1H), 7.77 (d, J=9 Hz, 1H), 7.54 (br, 4H), 7.35 (s, 1H), 6.95-6.92 (m, 1H), 3.87 (s, 3H, $OCH_3$). Calculated MS for $C_{18}H_{14}BrNO_2$, 355.02; observed, $(M+H)^+$ 356.3.

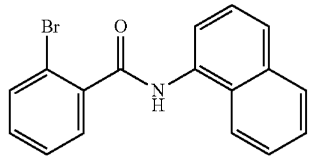 [SMILES: O=C(Nc1cccc2ccccc12)c1ccccc1Br]

Example 5: 2-bromo-N-(naphthalen-1-yl)benzamide: 2-Bromo-benzoic acid (0.0822 g, 0.4089 mmol), 1-aminonaphthalene (0.0644 g, 0.4497 mmol) and (2-(1H-benzotriazol-1-yl)-1,1,3,3-tetramethyluronium hexafluorophosphate) (HBTU, 0.1705 g, 0.4497 mmol) were dissolved in N,N-dimethylformamide (DMF, 1 mL) and treated with N,N-diisopropylethylamine (0.21 mL). The mixture was stirred at 22° C. for 18 hours. Ethyl acetate (20 mL) was added to dilute the mixture and the mixture was washed with HCl (5 mL, 1M, twice), saturated $NaHCO_3$ solution, and saturated brine, subsequently, concentrated under vacuum and purified using normal phase chromatography (12 g Isco silica column, Ethyl acetate-Hexane, 0~25%) to give a white solid (0.0296 g, 22.2%). $^1H$ NMR (300 MHz, $CDCl_3$): δ 8.16 (d, J=6 Hz, 1H), 8.06-8.02 (m, 2H), 7.92 (s, 1H), 7.79-7.69 (m, 3H), 7.56-7.46 (m, 4H), 7.41-7.38 (m, 1H). Calculated MS for $C_{17}H_{12}BrNO$, 325.01; observed, $(M+H)^+$ 326.3.

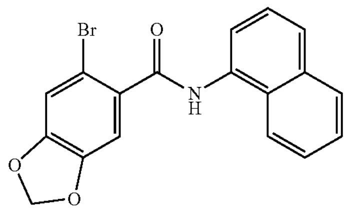 [SMILES: O=C(Nc1cccc2ccccc12)c1cc2c(cc1Br)OCO2]

Example 6: 6-bromo-N-(naphthalen-1-yl)benzo[d][1,3]dioxole-5-carboxamide: 6-Bromobenzo [d][1,3]dioxole-5-carboxylic acid (0.0550 g, 0.2245 mmol), 1-aminonaphthalene (0.0354 g, 0.2469 mmol) and (2-(1H-benzotriazol-1-yl)-1,1,3,3-tetramethyluronium hexafluorophosphate) (HBTU, 0.0936 g, 0.2469 mmol) were dissolved in N,N-dimethylformamide (DMF, 1 mL) and treated with N,N-diisopropylethylamine (0.12 mL). The mixture was stirred 22° C. for 18 hours. Ethyl acetate (20 mL) was added to dilute the mixture and washed with HCl (5 mL, 1M, twice), saturated $NaHCO_3$ solution, saturated brine, subsequently, concentrated under vacuum, and purified using normal phase chromatography (12 g Isco silica column, Ethyl acetate-Hexane, 0~15%) and further purification on HPLC [$H_2O$ (0.1% TFA)-$CH_3CN$ (0.1% TFA), 30%~90%, 15 minutes] to give a white solid (6.97 mg, 8.39%). $^1H$ NMR (300 MHz, $CDCl_3$): $^1H$ NMR (300 MHz, $CDCl_3$): δ 8.15-8.13 (m, 2H), 8.00 (d, J=6 Hz, 1H), 7.91-7.89 (m, 1H), 7.76 (d, J=9 Hz, 1H), 7.55-7.50 (m, 3H), 7.30 (s, 1H), 7.11 (s, 1H), 6.08 (s, 2H, $OCH_2O$). Calculated MS for $C_{18}H_{12}BrNO_3$, 369.00; observed, $(M+H)^+$ 370.3.

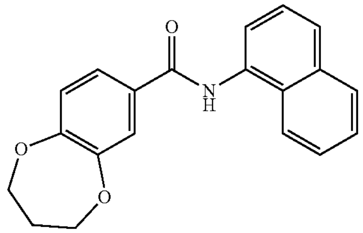 [SMILES: O=C(Nc1cccc2ccccc12)c1ccc2c(c1)OCCCO2]

Example 7: N-(naphthalen-1-yl)-3,4-dihydro-2H-benzo[b][1,4]dioxepine-7-Carboxamide: 3,4-Dihydro-2H-1,5-benzodioxepin-7-carboxylic acid (0.0842 g, 0.4336 mmol), 1-aminonaphthalene (0.0683 g, 0.4769 mmol) and (2-(1H-benzotriazol-1-yl)-1,1,3,3-tetramethyluronium hexafluorophosphate) (HBTU, 0.1809 g, 0.4769 mmol) were dissolved in N,N-dimethylformamide (DMF, 1 mL) and treated with N,N-diisopropylethylamine (0.23 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (12 g Isco silica column, Ethyl acetate-Hexane, 0~20%) and further purification on HPLC [$H_2O$ (0.1% TFA)-$CH_3CN$ (0.1% TFA), 30%~90%, 15 minutes] to give a white solid (0.0175 g, 12.66%). $^1H$ NMR (300 MHz, $CDCl_3$): δ 8.10 (s, 1H), 8.05-8.02 (m, 1H), 7.91-7.88 (m, 2H), 7.75-7.73 (m, 1H), 7.62-7.49 (m, 5H), 7.10-7.07 (m, 1H), 4.36-4.29 (m, 4H), 2.32-2.22 (m, 2H). Calculated MS for $C_{20}H_{17}NO_3$, 319.12; observed, $(M+H)^+$ 320.4.

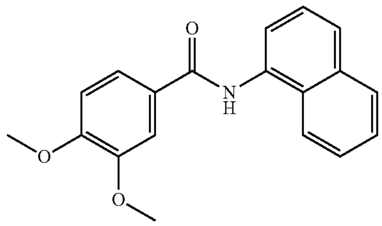 [SMILES: COc1ccc(C(=O)Nc2cccc3ccccc23)cc1OC]

Example 8: 3,4-dimethoxy-N-(naphthalen-1-yl)benzamide: 3,4-dimethoxybenzoic acid (0.0996 g, 0.5467 mmol), 1-aminonaphthalene (0.0861 g, 0.6013 mmol) and (2-(1H-benzotriazol-1-yl)-1,1,3,3-tetramethyluronium hexafluorophosphate) (HBTU, 0.2280 g, 0.6013 mmol) were dissolved in N,N-dimethylformamide (DMF, 1 mL) and treated with N,N-diisopropylethylamine (0.29 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (12 g Isco silica column, Ethyl acetate-Hexane, 0~30%) to give a white solid (0.009 g). $^1H$ NMR (300 MHz, $CDCl_3$): δ 8.17 (s, 1H), 8.03-8.00 (m, 1H), 7.92-7.89 (m, 2H), 7.77-7.74 (m, 1H), 7.59-7.50 (m, 4H), 6.98-6.95 (m, 1H), 3.98-3.94 (m, 6H). Calculated MS for $C_{19}H_{17}NO_3$, 307.12; observed, $(M+H)^+$ 308.4.

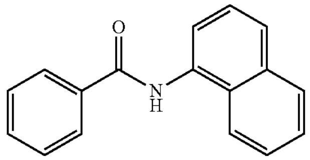 [SMILES: O=C(Nc1cccc2ccccc12)c1ccccc1]

Example 9: N-(naphthalen-1-yl)benzamide: 1-Amino-naphthalene (0.0667 g, 0.4658 mmol), and N,N-dimethylpyridin-4-amine (DMAP, 0.0086 g, 0.0705 mmol) were dissolved in pyridine (1 mL) and treated with benzoyl chloride (0.059 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (12 g gold silica column, Ethyl acetate-Hexane, 0~20%) give the desired produce (a white solid, 0.0374 g) $^1H$ NMR (300 MHz, $CDCl_3$): δ 8.20 (s, 1H), 8.08-7.92 (m, 5H), 7.77-7.75 (m, 1H), 7.61-7.51 (m, 6H). Calculated MS for $C_{17}H_{13}NO$, 247.10; observed, $(M+H)^+$ 248.4.

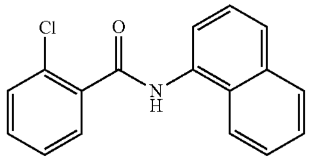 [SMILES: O=C(Nc1cccc2ccccc12)c1ccccc1Cl]

Example 10: 2-chloro-N-(naphthalen-1-yl)benzamide: 1-Amino-naphthalene (0.0548 g, 0.3827 mmol), and triethylamine ($NEt_3$, 0.16 mL, 1.1481 mmol) were dissolved in $CH_2Cl_2$ (1 mL) and treated with 2-chlorobenzoyl chloride (0.049 mL, 0.3827 mmol). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (12 g gold silica column, Ethyl acetate-Hexane, 0~15%) to give a mixture that was further purified on HPLC ($CH_3CN$ (0.1% TFA)-$H_2O$ (0.1% TFA), 30%~90% ($CH_3CN$ %), 15 minutes) to give the title compound (a white solid, 1.57 mg) $^1H$ NMR (300 MHz, $CDCl_3$): δ 8.35 (s, 1H), 8.15-8.14 (m, 1H), 8.01-7.92 (m, 3H), 7.78-7.75 (m, 1H), 7.55-7.47 (m, 6H). Calculated MS for $C_{17}H_{12}ClNO$, 281.06; observed, $(M+H)^+$ 282.3.

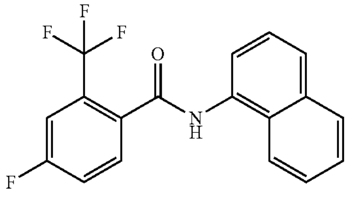 [SMILES: O=C(Nc1cccc2ccccc12)c1ccc(F)cc1C(F)(F)F]

Example 11: 4-fluoro-N-(naphthalen-1-yl)-2-(trifluoromethyl)benzamide: 1-Amino-naphthalene (0.0567 g, 0.3959 mmol), and triethylamine ($NEt_3$, 0.17 mL, 1.1877 mmol) were dissolved in $CH_2Cl_2$ (1 mL) and treated with 4-fluoro-2-(trifluoromethyl)-benzoyl chloride (0.0897 g, 0.3959 mmol). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (12 g gold silica column, Ethyl acetate-Hexane, 0~15%) to give a mixture that was further purified by HPLC ($CH_3CN$ (0.1% TFA)-$H_2O$ (0.1% TFA), 30%~90% ($CH_3CN$ %), 15 minutes) to give the title compound (a white solid, 3.53 mg) $^1H$ NMR (300 MHz, $CDCl_3$): δ 8.05-8.03 (m, 1H), 7.90-7.80 (m, 5H), 7.53 (s, 4H), 7.39 (s, 1H). Calculated MS for $C_{18}H_{11}F_4NO$, 333.08; observed, $(M+H)^+$ 334.4.

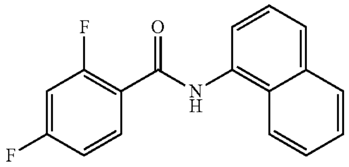 [SMILES: O=C(Nc1cccc2ccccc12)c1ccc(F)cc1F]

Example 12: 2,4-difluoro-N-(naphthalen-1-yl)benzamide: 1-Amino-naphthalene (0.0523 g, 0.3652 mmol), and triethylamine ($NEt_3$, 0.15 mL, 1.0956 mmol) were dissolved in $CH_2Cl_2$ (1 mL) and treated with 2,4-difluorobenzoyl chloride (0.045 mL, 0.3652 mmol). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (12 g gold silica column, Ethyl acetate-Hexane, 0~20%) provided the title product (0.0531 g, white solid) $^1H$ NMR (300 MHz, $CDCl_3$): δ 8.83 (d, J=15 Hz, 1H), 8.32-8.27 (m, 1H), 8.17 (d, J=6 Hz, 1H), 7.93-7.90 (m, 2H), 7.77-7.74 (m, 1H), 7.55 (s, 3H), 7.10-6.95 (m, 2H). Calculated MS for $C_{17}H_{11}F_2NO$, 283.08; observed, $(M+H)^+$ 284.4.

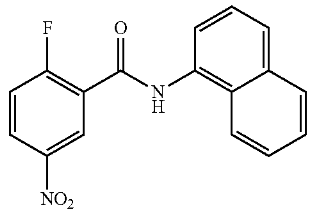 [SMILES: O=C(Nc1cccc2ccccc12)c1cc([N+](=O)[O-])ccc1F]

Example 13: 2-fluoro-N-(naphthalen-1-yl)-5-nitrobenzamide: 1-Amino-naphthalene (0.0586 g, 0.4092 mmol), and N,N-diisopropylethylamine ($(iPr)_2NEt$, 0.19 mL, 1.116 mmol) were dissolved in $CH_2Cl_2$ (2 mL) and treated with 2-fluoro-5-nitrobenzoyl chloride (0.0787 g, 0.3866 mmol). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, concentrated under vacuum and purified first with normal phase chromatography. (12 g Isco gold silica column, Ethyl acetate-Hexane, 0~20%) and then further purification on an HPLC ($CH_3CN$ (0.1% TFA)-$H_2O$ (0.1% TFA), 30%~90% ($CH_3CN$ %), 15 minutes) to give the title compound (11.48 mg, white solid). $^1H$ NMR (300 MHz, $CDCl_3$): δ 9.18 (s, 1H), 8.84 (d, J=15 Hz, 1H), 8.46 (s, 1H), 8.18 (s, 1H), 7.93 (d, J=6 Hz, 2H), 7.80 (d, J=6 Hz, 1H), 7.58-7.43 (m, 4H). Calculated MS for $C_{17}H_{11}FN_2O_3$, 310.08; observed, $(M+H)^+$ 311.3.

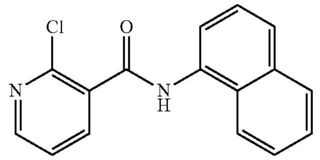 [SMILES: O=C(Nc1cccc2ccccc12)c1cccnc1Cl]

Example 14: 2-chloro-N-(naphthalen-1-yl)nicotinamide: 1-Amino-naphthalene (0.0663 g, 0.4630 mmol), and N,N-diisopropylethylamine ($(iPr)_2NEt$, 0.20 mL, 1.1616 mmol) were dissolved in $CH_2Cl_2$ (2 mL) and treated with 2-chloronicotinoyl chloride (0.0681 g, 0.3872 mmol). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (12 g gold silica column, Ethyl acetate-Hexane, 0~50%) to give the title compound (0.0118 g, white solid). $^1H$ NMR (300 MHz, $CDCl_3$): δ 8.66 (s, 1H), 8.56 (s, 1H), 8.35 (d, J=6 Hz, 1H), 8.11-7.77 (m, 4H), 7.56-7.45 (m, 4H). Calculated MS for $C_{16}H_{11}ClN_2O$, 282.06; observed, $(M+H)^+$ 283.3.

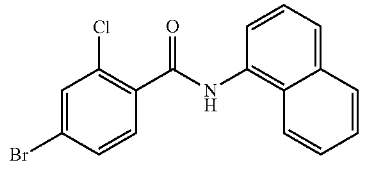

Example 15: 4-bromo-2-chloro-N-(naphthalen-1-yl)benzamide: 4-bromo-2-chlorobenzoic acid (0.0706 g, 0.2781 mmol), 1-aminonaphthalene (0.0438 g, 0.3058 mmol) and (2-(1H-benzotriazol-1-yl)-1,1,3,3-tetramethyluronium hexafluorophosphate) (HBTU, 0.1160 g, 0.3058 mmol) were dissolved in N,N-dimethylformamide (DMF, 1 mL) and treated with N,N-diisopropylethylamine (0.15 mL). The mixture was stirred at 22° C. for 18 hours. Ethyl acetate (20 mL) was added to dilute the mixture and washed with HCl (5 mL, 1M, twice), saturated $NaHCO_3$ solution, saturated brine, subsequently, concentrated under vacuum, and purified first with normal phase chromatography (12 g Isco silica column, Ethyl acetate-Hexane, 0~25%) and then further purification on HPLC ($CH_3CN$ (0.1% TFA)-$H_2O$ (0.1% TFA), 30%~90% ($CH_3CN$ %), 15 minutes) to give the title compound (a white solid, 0.0229 g). $^1H$ NMR (300 MHz, $CDCl_3$): δ 8.34 (s, 1H), 8.12 (d, J=9 Hz, 1H), 7.97-7.72 (m, 5H), 7.57 (s, 4H). Calculated MS for $C_{17}H_{11}BrClNO$, 358.97; observed, $(M+H)^+$ 360.3.

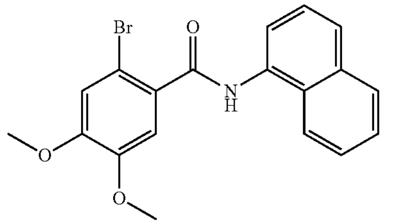 [SMILES: COc1cc(Br)c(C(=O)Nc2cccc3ccccc23)cc1OC]

Example 16: 2-bromo-4,5-dimethoxy-N-(naphthalen-1-yl)benzamide: 2-Bromo-4,5-dimethoxybenzoic acid (0.0701 g, 0.2685 mmol), 1-aminonaphthalene (0.0423 g, 0.2953 mmol) and (2-(1H-benzotriazol-1-yl)-1,1,3,3-tetramethyluronium hexafluorophosphate) (HBTU, 0.1119 g, 0.2953 mmol) were dissolved in N,N-dimethylformamide (DMF, 1 mL) and treated with N,N-diisopropylethylamine (0.14 mL). The mixture was stirred at 22° C. for 18 hours. Ethyl acetate (20 mL) was added to dilute the mixture and washed with HCl (5 mL, 1M, twice), saturated $NaHCO_3$ solution, saturated brine, subsequently, concentrated under vacuum, and then purified first with normal phase chromatography (12 g Isco silica column, Ethyl acetate-Hexane, 0~20%) and then further purification on HPLC ($CH_3CN$ (0.1% TFA)-$H_2O$ (0.1% TFA), 30%~90% ($CH_3CN$ %), 15 minutes) to give the title compound (a white solid, 0.0198 g). $^1H$ NMR (300 MHz, $CDCl_3$): δ 8.44 (s, 1H), 8.17 (d, J=6 Hz, 1H), 8.05 (d, J=9 Hz, 1H), 7.91 (d, J=9 Hz, 1H), 7.76 (d, J=9 Hz, 1H), 7.57-7.52 (m, 3H), 7.48 (s, 1H), 7.11 (s, 1H), 3.96 (s, 6H). Calculated MS for $C_{19}H_{16}BrNO_3$, 385.03; observed, $(M+H)^+$ 386.3.

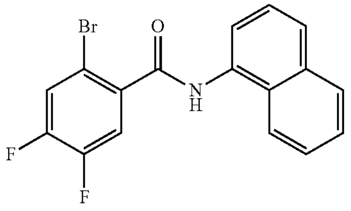 [SMILES: O=C(Nc1cccc2ccccc12)c1cc(F)c(F)cc1Br]

Example 17: 2-bromo-4,5-difluoro-N-(naphthalen-1-yl)benzamide: 2-Bromo-4,5-didifluorobenzoic acid (0.0885 g, 0.3734 mmol), 1-aminonaphthalene (0.0588 g, 0.4107 mmol) and (2-(1H-benzotriazol-1-yl)-1,1,3,3-tetramethyluronium hexafluorophosphate) (HBTU, 0.1558 g, 0.4107 mmol) were dissolved in N,N-dimethylformamide (DMF, 1 mL) and treated with N,N-diisopropylethylamine (0.20 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (12 g Isco silica column, Ethyl acetate-Hexane, 0~20%) to give the title compound (a white solid, 0.0408 g). $^1H$ NMR (300 MHz, $CDCl_3$): δ 8.14-8.10 (m, 2H), 7.99-7.91 (m, 2H), 7.81-7.69 (m, 2H), 7.57-7.52 (m, 4H). Calculated MS for $C_{17}H_{10}BrF_2NO$, 360.99; observed, $(M+H)^+$ 362.3.

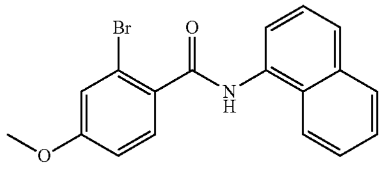 [SMILES: COc1ccc(C(=O)Nc2cccc3ccccc23)c(Br)c1]

Example 18: 2-bromo-4-methoxy-N-(naphthalen-1-yl)benzamide: 2-bromo-4-methoxy benzoic acid (0.0677 g, 0.293 mmol), 1-aminonaphthalene (0.0462 g, 0.3223 mmol, 1.1 equiv.) and (2-(1H-benzotriazol-1-yl)-1,1,3,3-tetramethyluronium hexafluorophosphate) (HBTU, 0.1222 g, 0.3223 mmol, 1.1 equiv.) were dissolved in N,N-dimethylformamide (DMF, 1 mL) and treated with N,N-diisopropylethylamine (0.15 mL, 3 equiv.). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, Ethyl acetate %: 0~20%) and further purified on HPLC ($H_2O$ (0.1% TFA)-$CH_3CN$ (0.1% TFA), $H_2O$ %: 90%~10%) gave a white solid (0.0116 g). $^1H$ NMR (300 MHz, $CDCl_3$): δ 8.24-8.16 (m, 2H), 8.01 (s, 1H), 7.91-7.74 (m, 3H), 7.24 (s, 3H), 7.21 (s, 1H), 7.00 (s, 1H), 3.88 (s, 3H). Calculated MS for $C_{18}H_{14}BrNO_2$, 355.02; observed, $(M+H)^+$ 356.3.

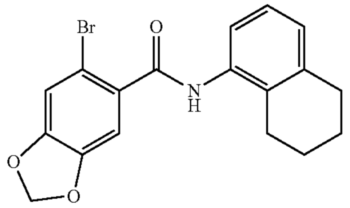 [SMILES: O=C(Nc1cccc2c1CCCC2)c1cc2c(cc1Br)OCO2]

Example 19: 6-bromo-N-(5,6,7,8-tetrahydronaphthalen-1-yl)benzo[d][1,3]dioxole-5-carboxamide: 5,6,7,8-tetrahydronaphthalen-1-amine (0.021 g, 0.14 mmol, 1.1 eq) and N,N-diisopropylethylamine (0.07 mL, 0.39 mmole, 3 eq) were dissolved in dichloromethane (1 mL). Then 6-bromo-1,3-benzodioxide-5-carbonyl chloride (0.1349 mmol/mL $CH_2Cl_2$ prepared in situ, 1 eq) was added to the above solution. The mixture was stirred at 22° C. for 18 hours. Ethyl acetate (20 mL) was added to dilute the mixture and washed with HCl (1M, 5 mL, twice), saturated $NaHCO_3$ solution, and saturated brine, subsequently, and concentrated. Purification on ISCO (4 g silica column, Ethyl acetate-Hexane, Ethyl acetate %: 0~20%) gave a white solid (0.0289 g). $^1H$ NMR (300 MHz, $CDCl_3$): δ 7.84 (s, 1H), 7.49 (s, 1H), 7.18-7.15 (m, 2H), 7.06 (s, 1H), 6.97-6.94 (m, 1H), 6.05 (s, 2H, $OCH_2O$), 2.80-2.78 (m, 2H), 2.68-2.66 (m, 2H), 1.84-1.79 (m, 4H). Calculated MS for $C_{18}H_{16}BrNO_3$, 373.03; observed, $(M+H)^+$ 374.3.

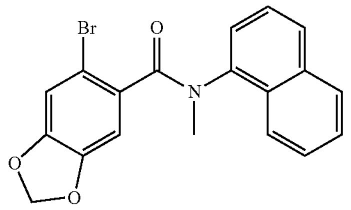 [SMILES: CN(C(=O)c1cc2c(cc1Br)OCO2)c1cccc2ccccc12]

Example 20: 6-bromo-N-methyl-N-(naphthalen-1-yl) benzo[d][1,3]dioxole-5-carboxamide: The method is as the same to that for the synthesis of example 19. Purification on ISCO (4 g silica column, Ethyl acetate-Hexane, 0~25%) gave a white solid (0.035 g). $^1$H NMR (300 MHz, $CDCl_3$): δ 7.98 (d, J=9 Hz, 1H), 7.85 (d, J=9 Hz, 1H), 7.73 (d, J=9 Hz, 1H), 7.65-7.50 (m, 4H), 6.79 (s, 1H), 6.39 (s, 1H), 5.76 (s, 1H, $OCH_2O$), 5.71 (s, 1H, $OCH_2O$), 3.54 (s, 3H, $NCH_3$). Calculated MS for $C_{19}H_{14}BrNO_3$, 383.02; observed, $(M+H)^+$ 384.4.

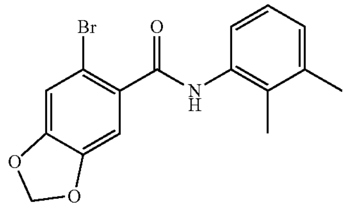 [SMILES: Cc1cccc(NC(=O)c2cc3c(cc2Br)OCO3)c1C]

Example 21: 6-bromo-N-(2,3-dimethylphenyl)benzo[d][1,3]dioxole-5-carboxamide: The method is as the same to that for the synthesis of example 19. Purification on ISCO (4 g silica column, Ethyl acetate-Hexane, 0~25%) gave a white solid (0.0334 g). $^1$H NMR (300 MHz, $CDCl_3$): δ 7.65 (d, J=6 Hz, 1H), 7.54 (s, 1H), 7.20-7.13 (m, 2H), 7.07 (s, 2H), 6.06 (s, 2H, $OCH_2O$), 2.33 (s, 3H, $CH_3$), 2.25 (s, 3H, $CH_3$). Calculated MS for $C_{16}H_{14}BrNO_3$, 347.02; observed, $(M+H)^+$ 348.3.

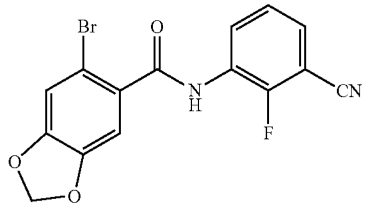 [SMILES: N#Cc1cccc(NC(=O)c2cc3c(cc2Br)OCO3)c1F]

Example 22: 6-bromo-N-(3-cyano-2-fluorophenyl)benzo[d][1,3]dioxole-5-carboxamide: The method is as the same to that for the synthesis of example 19. Purification on ISCO (4 g silica column, Ethyl acetate-Hexane, 0~25%) gave a white solid (0.0334 g). $^1$H NMR (300 MHz, $CDCl_3$): δ 8.80-8.75 (m, 1H), 8.17 (s, 1H), 7.39-7.21 (m, 4H), 6.09 (s, 2H, $OCH_2O$). Calculated MS for $C_{15}H_8BrFN_2O_3$, 361.97; observed, $(M+H)^+$ 363.2.

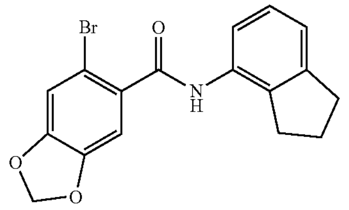 [SMILES: O=C(Nc1cccc2c1CCC2)c1cc2c(cc1Br)OCO2]

Example 23: 6-bromo-N-(2,3-dihydro-1H-inden-4-yl) benzo[d][1,3]dioxole-5-carboxamide: The method is as the same to that for the synthesis of example 19. Purification on ISCO (4 g silica column, Ethyl acetate-Hexane, Ethyl acetate %: 0~20%) gave a white solid (0.0313 g). $^1$H NMR (300 MHz, $CDCl_3$): δ 7.94 (d, J=6 Hz, 1H), 7.62 (s, 1H), 7.22-7.19 (m, 2H), 7.08-7.06 (m, 2H), 6.06 (s, 2H, $OCH_2O$), 3.00-2.90 (m, 4H), 2.16-2.09 (m, 2H). Calculated MS for $C_{17}H_{14}BrNO_3$, 359.02; observed, $(M+H)^+$ 360.3.

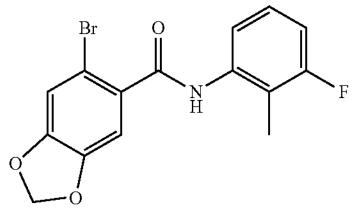 [SMILES: Cc1c(F)cccc1NC(=O)c1cc2c(cc1Br)OCO2]

Example 24: 6-bromo-N-(3-fluoro-2-methylphenyl) benzo[d][1,3]dioxole-5-carboxamide: The method is as the same to that for the synthesis of example 19. Purification on ISCO (4 g silica column, Ethyl acetate-Hexane, 0~20%) gave a white solid (0.0273 g). $^1$H NMR (300 MHz, $CDCl_3$): δ 7.79 (s, 1H), 7.61 (s, 1H), 7.26-7.21 (m, 2H), 7.07 (s, 1H), 6.94-6.89 (m, 1H), 6.06 (s, 2H, $OCH_2O$), 2.25 (s, 3H, $CH_3$). Calculated MS for $C_{15}H_{11}BrFNO_3$, 350.99; observed, $(M+H)^+$ 352.3.

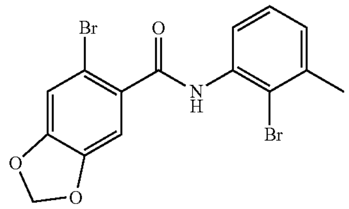 [SMILES: Cc1cccc(NC(=O)c2cc3c(cc2Br)OCO3)c1Br]

Example 25: 6-bromo-N-(2-bromo-3-methylphenyl) benzo[d][1,3]dioxole-5-carboxamide: The method is as the same to that for the synthesis of example 19. Purification on ISCO (4 g silica column, Ethyl acetate-Hexane, 0~20%) gave a white solid (0.0273 g). $^1$H NMR (300 MHz, $CDCl_3$): δ 8.33-8.27 (m, 2H), 7.16 (s, 1H), 7.08-7.04 (m, 2H), 6.07 (s, 2H, $OCH_2O$), 2.45 (s, 3H, $CH_3$). Calculated MS for $C_{15}H_{11}Br_2NO_3$, 410.91; observed, $(M+H)^+$ 412.2.

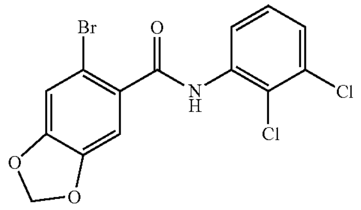 [SMILES: O=C(Nc1cccc(Cl)c1Cl)c1cc2c(cc1Br)OCO2]

Example 26: 6-bromo-N-(2,3-dichlorophenyl)benzo[d][1,3]dioxole-5-carboxamide: The method is as the same to that for the synthesis of example 19. Purification on ISCO (4 g silica column, Ethyl acetate-Hexane, 0~20%) gave a yellow solid (0.0363 g). $^1$H NMR (300 MHz, $CDCl_3$): δ 8.49 (s, 1H), 8.32 (s, 1H), 7.17 (s, 1H), 7.08 (s, 1H), 6.07 (s, 2H, $OCH_2O$). Calculated MS for $C_{14}H_8BrClNO_3$, 386.91; observed, $(M+H)^+$ 388.2.

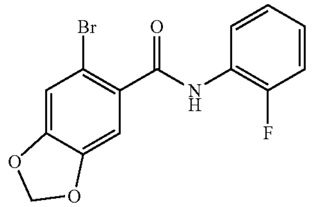 [SMILES: O=C(Nc1ccccc1F)c1cc2c(cc1Br)OCO2]

Example 27: 6-bromo-N-(2-fluorophenyl)benzo[d][1,3]dioxole-5-carboxamide: The method is as the same to that for the synthesis of example 19. Purification on ISCO (4 g silica column, Ethyl acetate-Hexane, 0~20%) gave a white solid (0.024 g). $^1$H NMR (300 MHz, $CDCl_3$): δ 8.49-8.44 (m, 1H), 8.02 (s, 1H), 7.20-7.07 (m, 5H), 6.07 (s, 2H, $OCH_2O$). Calculated MS for $C_{14}H_9BrFNO_3$, 336.97; observed, $(M+H)^+$ 338.3.

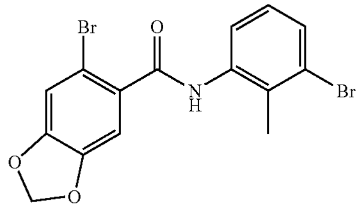 [SMILES: Cc1c(Br)cccc1NC(=O)c1cc2c(cc1Br)OCO2]

Example 28: 6-bromo-N-(3-bromo-2-methylphenyl)benzo[d][1,3]dioxole-5-carboxamide: The method is as the same to that for the synthesis of example 19. Purification on ISCO (4 g silica column, Ethyl acetate-Hexane, 0~20%) gave a white solid (0.0301 g). $^1$H NMR (300 MHz, $CDCl_3$): δ 7.86-7.83 (m, 1H), 7.62 (s, 1H), 7.45 (d, J=6 Hz, 1H), 7.19-7.06 (m, 3H), 6.06 (s, 2H, $OCH_2O$), 2.44 (s, 3H, $CH_3$). Calculated MS for $C_{15}H_{11}Br_2NO_3$, 410.9; observed, $(M+H)^+$ 412.2.

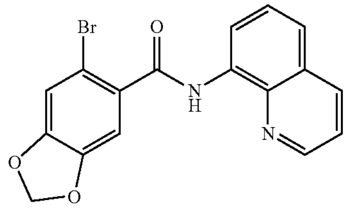 [SMILES: O=C(Nc1cccc2cccnc12)c1cc2c(cc1Br)OCO2]

Example 29: 6-bromo-N-(quinolin-8-yl)benzo[d][1,3]dioxole-5-carboxamide: The method is as the same to that for the synthesis of example 19. Purification on ISCO (4 g silica column, Ethyl acetate-Hexane, 0~20%) gave a white solid (0.0386 g). $^1$H NMR (300 MHz, $CDCl_3$): δ 10.30 (s, 1H), 8.92-8.90 (m, 1H), 8.80 (s, 1H), 8.18 (d, J=6 Hz, 1H), 7.59-7.54 (m, 2H), 7.48-7.44 (m, 1H), 7.21 (s, 1H), 7.11 (s, 1H), 6.07 (s, 2H, $OCH_2O$). Calculated MS for $C_{17}H_{11}BrN_2O_3$, 370.00; observed, $(M+H)^+$ 371.3.

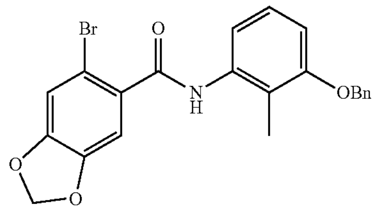 [SMILES: Cc1c(NC(=O)c2cc3c(cc2Br)OCO3)cccc1OCc1ccccc1]

Example 30: N-(3-(benzyloxy)-2-methylphenyl)-6-bromobenzo[d][1,3]dioxole-5-carboxamide: The method is as the same to that for the synthesis of example 19. Purification on ISCO (4 g silica column, Ethyl acetate-Hexane, 0~20%) gave a white solid (0.0386 g). $^1$H NMR (300 MHz, $CDCl_3$): δ 7.62-7.56 (m, 2H), 7.43-7.32 (m, 5H), 7.20 (s, 2H), 7.06 (s, 1H), 6.83-6.80 (m, 1H), 6.05 (s, 2H, $OCH_2O$), 5.10 (s, 2H, $PhCH_2$), 2.27 (s, 3H, $CH_3$). Calculated MS for $C_{22}H_{18}BrNO_4$, 439.04; observed, $(M+H)^+$ 440.4.

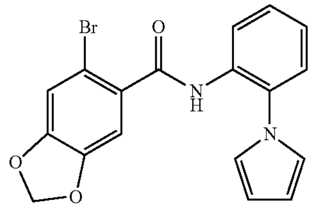 [SMILES: O=C(Nc1ccccc1-n1cccc1)c1cc2c(cc1Br)OCO2]

Example 31: N-(2-(1H-pyrrol-1-yl)phenyl)-6-bromobenzo[d][1,3]dioxole-5-carboxamide: The method is as the same to that for the synthesis of example 19. Purification on ISCO (4 g silica column, Ethyl acetate-Hexane, 0~20%) gave a white solid (0.0258 g). $^1$H NMR (300 MHz, $CDCl_3$): δ 8.57 (d, J=9 Hz, 1H), 7.75 (s, 1H), 7.47-7.42 (m, 2H), 7.33-7.18 (m, 3H), 7.05 (s, 1H), 6.97 (s, 1H), 6.82 (s, 2H), 6.02 (s, 2H, $OCH_2O$). Calculated MS for $C_{18}H_{13}BrN_2O_3$, 384.01; observed, $(M+H)^+$ 385.3.

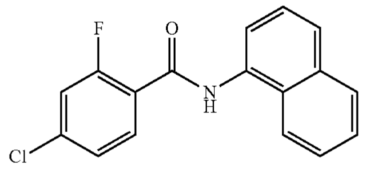 [SMILES: O=C(Nc1cccc2ccccc12)c1ccc(Cl)cc1F]

Example 32: 4-chloro-2-fluoro-N-(naphthalen-1-yl)benzamide: 4-chloro-2-fluorobenzoic acid (0.0349 g, 0.20 mmol), 1-aminonaphthalene (0.037 g, 0.258 mmol) and (2-(1H-benzotriazol-1-yl)-1,1,3,3-tetramethyluronium hexafluorophosphate) (HBTU, 0.0874 g, 0.2305 mmol) were dissolved in N,N-dimethylformamide (DMF, 1 mL) and treated with N,N-diisopropylethylamine (0.038 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a white solid (0.0066 g, 11.0%). $^1$H NMR (300 MHz, $CDCl_3$): δ 8.34 (s, 1H), 8.12 (d, J=9 Hz, 1H), 8.0-7.90 (m, 3H), 7.77 (d, J=9 Hz, 1H), 7.59-7.51 (m, 3H), 7.28 (s, 1H), 7.20-7.13 (m, 1H). Calculated MS for $C_{17}H_{11}ClFNO$, 299.05; observed, $(M+H)^+$ 300.3.

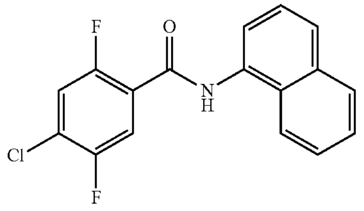 [SMILES: O=C(Nc1cccc2ccccc12)c1cc(F)c(Cl)cc1F]

Example 33: 4-chloro-2,5-difluoro-N-(naphthalen-1-yl) benzamide: 4-chloro-2,5-difluorobenzoic acid (0.0397 g, 0.20 mmol), 1-aminonaphthalene (0.037 g, 0.258 mmol) and (2-(1H-benzotriazol-1-yl)-1,1,3,3-tetramethyluronium hexafluorophosphate) (HBTU, 0.0841 g, 0.2218 mmol) were dissolved in N,N-dimethylformamide (DMF, 1 mL) and treated with N,N-diisopropylethylamine (0.04 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a white needle crystal (0.0150 g, 22.9%). $^1$H NMR (300 MHz, $CDCl_3$): δ 8.86 (d, J=15 Hz, 1H), 8.16 (d, J=9 Hz, 1H), 8.09-8.04 (m, 1H), 7.91 (d, J=9 Hz, 2H), 7.77 (d, J=9 Hz, 1H), 7.61-7.52 (m, 3H), 7.38 (dd, J=12 Hz, 6 Hz, 1H). Calculated MS for $C_{17}H_{10}ClF_2NO$, 317.04; observed, $(M+H)^+$ 318.3.

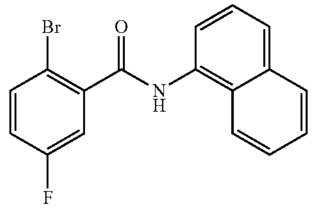 [SMILES: O=C(Nc1cccc2ccccc12)c1cc(F)ccc1Br]

Example 34: 2-bromo-5-fluoro-N-(naphthalen-1-yl)benzamide: 2-bromo-5-fluorobenzoic acid (0.0375 g, 0.17 mmol), 1-aminonaphthalene (0.037 g, 0.258 mmol) and (2-(1H-benzotriazol-1-yl)-1,1,3,3-tetramethyluronium hexafluorophosphate) (HBTU, 0.0746 g, 0.1967 mmol) were dissolved in N,N-dimethylformamide (DMF, 1 mL) and treated with N,N-diisopropylethylamine (0.033 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a white needle crystal (0.0492 g, 83.5%). $^1$H NMR (300 MHz, $CDCl_3$): δ 8.13-8.11 (m, 2H), 7.99 (d, J=9 Hz, 1H), 7.93-7.90 (m, 1H), 7.79 (d, J=9 Hz, 1H), 7.67 (dd, J=9 Hz, 3 Hz, 1H), 7.59-7.52 (m, 4H), 7.12 (dt, J=9 Hz, 3 Hz, 1H). Calculated MS for $C_{17}H_{11}BrFNO$, 343.00; observed, $(M+H)^+$ 345.3.

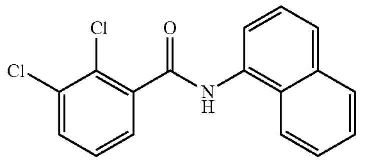 [SMILES: O=C(Nc1cccc2ccccc12)c1cccc(Cl)c1Cl]

Example 35: 2,3-dichloro-N-(naphthalen-1-yl)benzamide: 2,3-dichlorobenzoic acid (0.0319 g, 0.167 mmol), 1-aminonaphthalene (0.037 g, 0.258 mmol) and (2-(1H-benzotriazol-1-yl)-1,1,3,3-tetramethyluronium hexafluorophosphate) (HBTU, 0.0759 g, 0.2000 mmol) were dissolved in N,N-dimethylformamide (DMF, 1 mL) and treated with N,N-diisopropylethylamine (0.032 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a white solid (0.0361 g, 68.4%). $^1$H NMR (300 MHz, $CDCl_3$): δ 8.14-8.07 (m, 2H), 7.95-7.90 (m, 2H), 7.79-7.71 (m, 2H), 7.65-7.51 (m, 4H), 7.38 (t, J=9 Hz, 1H). Calculated MS for $C_{17}H_{11}Cl_2NO$, 315.02; observed, $(M+H)^+$ 316.3.

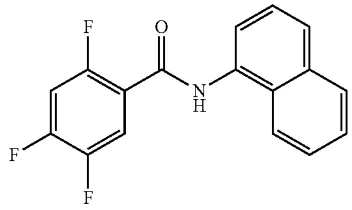 [SMILES: O=C(Nc1cccc2ccccc12)c1cc(F)c(F)cc1F]

Example 36: 2,4,5-trifluoro-N-(naphthalen-1-yl)benzamide: 2,4,5-trifluorobenzoic acid (0.0402 g, 0.2282 mmol), 1-aminonaphthalene (0.037 g, 0.258 mmol) and (2-(1H-benzotriazol-1-yl)-1,1,3,3-tetramethyluronium hexafluorophosphate) (HBTU, 0.0964 g, 0.2542 mmol) were dissolved in N,N-dimethylformamide (DMF, 1 mL) and treated with N,N-diisopropylethylamine (0.044 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a white solid (0.0094 g, 13.8%). $^1$H NMR (300 MHz, $CDCl_3$): δ 8.84 (d, J=15 Hz, 1H), 8.16-8.08 (m, 2H), 7.93-7.90 (m, 2H), 7.78-7.75 (m, 1H), 7.60-7.51 (m, 3H), 7.19-7.10 (m, 1H). Calculated MS for $C_{17}H_{10}F_3NO$, 301.07; observed, $(M+H)^+$ 302.4.

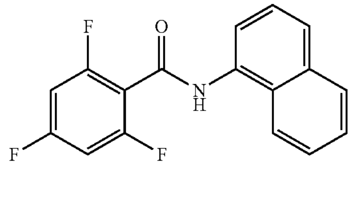 [SMILES: O=C(Nc1cccc2ccccc12)c1c(F)cc(F)cc1F]

Example 37: 2,4,6-trifluoro-N-(naphthalen-1-yl)benzamide: 2,4,6-trifluorobenzoic acid (0.0421 g, 0.2390 mmol), 1-aminonaphthalene (0.037 g, 0.258 mmol) and (2-(1H-benzotriazol-1-yl)-1,1,3,3-tetramethyluronium hexafluorophosphate) (HBTU, 0.1019 g, 0.2687 mmol) were dissolved in N,N-dimethylformamide (DMF, 1 mL) and treated with N,N-diisopropylethylamine (0.046 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a white solid (0.025 g, 34.7%). $^1$H NMR (300 MHz, $CDCl_3$): δ 8.06 (d, J=9 Hz, 1H), 7.94-7.90 (m, 3H), 7.79 (d, J=9 Hz, 1H), 7.60-7.51 (m, 3H), 6.84 (t, J=9 Hz, 2H). Calculated MS for $C_{17}H_{10}F_3NO$, 301.07; observed, $(M+H)^+$ 302.3.

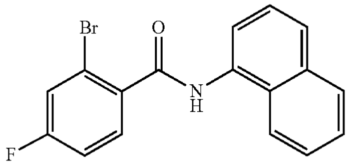 [SMILES: O=C(Nc1cccc2ccccc12)c1ccc(F)cc1Br]

Example 38: 2-bromo-4-fluoro-N-(naphthalen-1-yl)benzamide: 2-bromo-4-fluorobenzoic acid (0.0314 g, 0.1433 mmol), 1-aminonaphthalene (0.037 g, 0.258 mmol) and (2-(1H-benzotriazol-1-yl)-1,1,3,3-tetramethyluronium hexafluorophosphate) (HBTU, 0.0605 g, 0.1595 mmol) were dissolved in N,N-dimethylformamide (DMF, 1 mL) and treated with N,N-diisopropylethylamine (0.027 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a white solid (0.0164 g, 33.3%). $^1$H NMR (300 MHz, $CDCl_3$): δ 8.14-8.07 (m, 2H), 7.98 (d, J=9 Hz, 1H), 7.92-7.76 (m, 3H), 7.57-7.51 (m, 3H), 7.44 (d, J=9 Hz, 1H), 7.22-7.17 (m, 1H). Calculated MS for $C_{17}H_{11}BrFNO$, 343.0; observed, $(M+H)^+$ 344.3.

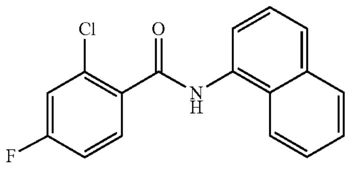 [SMILES: O=C(Nc1cccc2ccccc12)c1ccc(F)cc1Cl]

Example 39: 2-chloro-4-fluoro-N-(naphthalen-1-yl)benzamide: 2-chloro-4-fluorobenzoic acid (0.0421 g, 0.2411 mmol), 1-aminonaphthalene (0.037 g, 0.258 mmol) and (2-(1H-benzotriazol-1-yl)-1,1,3,3-tetramethyluronium hexafluorophosphate) (HBTU, 0.1085 g, 0.2861 mmol) were dissolved in N,N-dimethylformamide (DMF, 1 mL) and treated with N,N-diisopropylethylamine (0.046 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a white solid (0.0473 g, 65.4%). $^1$H NMR (300 MHz, $CDCl_3$): δ 8.85 (d, J=15 Hz, 1H), 8.27-8.17 (m, 2H), 7.95-7.90 (m, 2H), 7.76-7.75 (m, 1H), 7.60-7.51 (m, 3H), 7.38-7.29 (m, 2H). Calculated MS for $C_{17}H_{11}ClFNO$, 299.05; observed, $(M+H)^+$ 300.3.

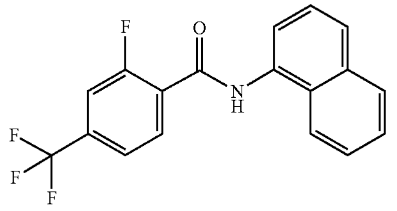 [SMILES: O=C(Nc1cccc2ccccc12)c1ccc(C(F)(F)F)cc1F]

Example 40: 2-fluoro-N-(naphthalen-1-yl)-4-(trifluoromethyl)benzamide: 2-fluoro3-(trifluoromethyl)benzoic acid (0.0357 g, 0.1715 mmol), 1-aminonaphthalene (0.037 g, 0.258 mmol) and (2-(1H-benzotriazol-1-yl)-1,1,3,3-tetramethyluronium hexafluorophosphate) (HBTU, 0.0739 g, 0.1949 mmol) were dissolved in N,N-dimethylformamide (DMF, 1 mL) and treated with N,N-diisopropylethylamine (0.033 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a white solid (0.0483 g, 65.4%). $^1$H NMR (300 MHz, $CDCl_3$): δ 8.85 (d, J=15 Hz, 1H), 8.27-8.17 (m, 2H), 7.95-7.90 (m, 2H), 7.76-7.75 (m, 1H), 7.60-7.51 (m, 3H), 7.38-7.29 (m, 2H). Calculated MS for $C_{18}H_{11}F_4NO$, 333.08; observed, $(M+H)^+$ 334.4.

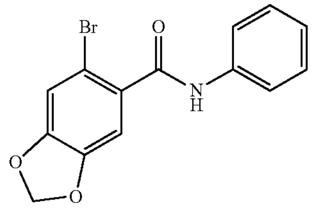 [SMILES: O=C(Nc1ccccc1)c1cc2c(cc1Br)OCO2]

Example 41: 6-bromo-N-phenylbenzo[d][1,3]dioxole-5-carboxamide: Aniline (0.0776 g, 0.8332 mmol) and N,N-diisopropylethylamine (0.04 mL) were dissolved in dichloromethane (1 mL). Then 6-bromo-1,3-benzodioxide-5-carbonyl chloride (1 mL, 0.0697 mmol/mL) was added to the above solution. The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~25%) gave a white solid (0.0165 g). $^1$H NMR (300 MHz, $CDCl_3$): δ 7.67-7.61 (m, 3H), 7.40-7.35 (m, 2H), 7.19-7.14 (m, 2H), 7.05 (s, 1H), 6.05 (s, 2H, $OCH_2O$). Calculated MS for $C_{14}H_{10}BrNO_3$, 318.98; observed, $(M+H)^+$ 322.3.

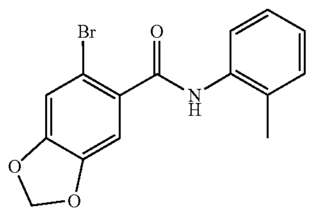

Example 42: 6-bromo-N-(o-tolyl)benzo[d][1,3]dioxole-5-carboxamide: The title compound was prepared according to the method of example 41 except that Aniline was replaced with 2-methyl-aniline. Purification on ISCO (4 g Isco silica column, Ethyl acetate-Hexane, Ethyl acetate %: 0~25%) gave a white solid (0.01436 g). $^1$H NMR (300 MHz, $CDCl_3$): δ 7.99 (d, J=6 Hz, 1H), 7.57 (s, 1H), 7.29-7.21 (m, 3H), 7.15-7.10 (m, 1H), 7.07 (s, 1H), 6.06 (s, 2H, $OCH_2O$), 2.35 (s, 3H, $CH_3$). Calculated MS for $C_{15}H_{12}BrNO_3$, 333.00; observed, $(M+H)^+$ 334.3.

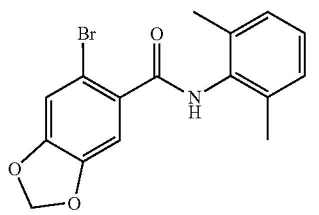 [SMILES: Cc1cccc(C)c1NC(=O)c1cc2c(cc1Br)OCO2]

Example 43: 6-bromo-N-(2,6-dimethylphenyl)benzo[d][1,3]dioxole-5-carboxamide: The title compound was prepared according to the method of example 41 except that Aniline was replaced with 2, 6-dimethyl-aniline. Purification on ISCO (4 g silica column, Ethyl acetate-Hexane, Ethyl acetate %: 0~25%) gave a white solid (0.01725 g). $^1$H NMR (300 MHz, $CDCl_3$): δ 7.21 (s, 1H), 7.15-7.10 (m, 3H), 7.08 (s, 1H), 6.06 (s, 2H, $OCH_2O$), 2.35 (s, 2×3H, $CH_3$). Calculated MS for $C_{16}H_{14}BrNO_3$, 347.02; observed, $(M+H)^+$ 348.3.

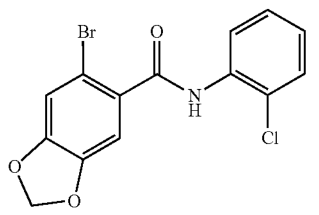

Example 44: 6-bromo-N-(2-chlorophenyl)benzo[d][1,3]dioxole-5-carboxamide: The title compound was prepared according to the method of example 41 except that Aniline was replaced with 2-chloroaniline. Purification on ISCO (4 g silica column, Ethyl acetate-Hexane, Ethyl acetate %: 0~25%) gave a white solid (0.0166 g). $^1$H NMR (300 MHz, $CDCl_3$): δ 8.53 (d, J=9 Hz, 1H), 8.24 (s, 1H), 7.43-7.40 (m, 1H), 7.36-7.31 (m, 1H), 7.18 (s, 1H), 7.13-7.06 (m, 2H), 6.07 (s, 2H, $OCH_2O$). Calculated MS for $C_{14}H_9BrClNO_3$, 352.94; observed, $(M+H)^+$ 354.2.

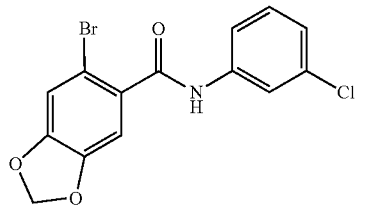 [SMILES: O=C(Nc1cccc(Cl)c1)c1cc2c(cc1Br)OCO2]

Example 45: 6-bromo-N-(3-chlorophenyl)benzo[d][1,3]dioxole-5-carboxamide: The title compound was prepared according to the method of example 41 except that Aniline was replaced with 3-chloroaniline. Purification on ISCO (4 g silica column, Ethyl acetate-Hexane, Ethyl acetate %: 0~25%) gave a white solid (0.0096 g). $^1$H NMR (300 MHz, $CDCl_3$): δ 7.76 (s, 1H), 7.69 (s, 1H), 7.46 (d, J=6 Hz, 1H), 7.32-7.26 (m, 1H), 7.21-7.13 (m, 2H), 7.06 (s, 1H), 6.06 (s, 2H, $OCH_2O$). Calculated MS for $C_{14}H_9BrClNO_3$, 352.94; observed, $(M+H)^+$ 354.3.

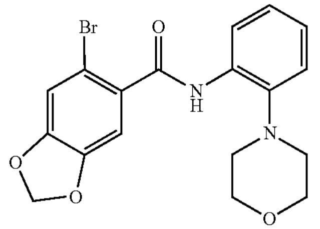 [SMILES: O=C(Nc1ccccc1N1CCOCC1)c1cc2c(cc1Br)OCO2]

Example 57: 6-bromo-N-(2-morpholinophenyl)benzo[d][1,3]dioxole-5-carboxamide: The title compound was prepared according to the method of example 41 except that Aniline was replaced with 2-morpholino-aniline. Purification on ISCO (4 g silica column, Ethyl acetate-Hexane, Ethyl acetate %: 0~25%) gave a white solid (0.01896 g). $^1$H NMR (300 MHz, $CDCl_3$): δ 9.18 (s, 1H), 8.57-8.54 (m, 1H), 7.26-7.22 (m, 2H), 7.16-7.10 (m, 2H), 7.08 (s, 1H), 6.07 (s, 2H, $OCH_2O$), 3.83 (t, J=6 Hz, 4H, $NCH_2CH_2O$), 2.90 (t, J=6 Hz, 4H, $NCH_2CH_2O$). Calculated MS for $C_{18}H_{17}BrN_2O_4$, 404.04; observed, $(M+H)^+$ 405.4.

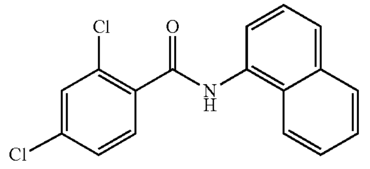 [SMILES: O=C(Nc1cccc2ccccc12)c1ccc(Cl)cc1Cl]

Example 47: 2,4-dichloro-N-(naphthalen-1-yl)benzamide: 2,4-Dichlorobenzoyl chloride (0.0446 g, 0.2129 mmol) and 1-aminonaphthalene (0.0842 g, 0.5880 mmol) were dissolved in dichloromethane (1 mL) and treated with N,N-diisopropylethylamine (0.11 mL). The mixture was stirred at 22° C. for 18 hours. A lot of white solid precipitated. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) and further purified on HPLC ($CH_3CN$—$H_2O$, 20%~95%, 17 min, 15 mL/min) to give object as light pink solid (6.64 mg). $^1$H NMR (300 MHz, $CDCl_3$): δ 8.34 (s, 1H), 8.12 (d, J=9 Hz, 1H), 7.98-7.89 (m, 3H), 7.78 (d, J=6 Hz, 1H), 7.61-7.51 (m, 4H), 7.43 (d, J=9 Hz, 1H). Calculated MS for $C_{17}H_{11}C_{12}NO$, 315.02; observed, $(M+H)^+$ 316.3.

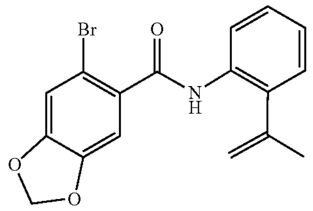 [SMILES: C=C(C)c1ccccc1NC(=O)c1cc2c(cc1Br)OCO2]

Example 48: 6-bromo-N-(2-(prop-1-en-2-yl)phenyl)benzo[d][1,3]dioxole-5-carboxamide: 2-(prop-1-en-2-yl)aniline (0.0824 g, 0.6187 mmol) and N,N-diisopropylethylamine (0.04 mL) were dissolved in dichloromethane (1 mL). Then 6-bromo-1,3-benzodioxide-5-carbonyl chloride (1 mL, 0.0697 mmol/mL) was added to the above solution. The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~25%) gave a yellowish oil (0.0148 g). $^1H$ NMR (300 MHz, $CDCl_3$): δ 8.45 (d, J=9 Hz, 1H), 8.07 (s, 1H), 7.35-7.30 (m, 1H), 7.20-7.10 (m, 3H), 7.05 (s, 1H), 6.05 (s, 2H, $OCH_2O$), 5.37-5.35 (m, 1H), 5.06-5.04 (m, 1H), 2.08-2.07 (m, 3H, $CH_3$). Calculated MS for $C_{17}H_{14}BrNO_3$, 359.02; observed, $(M+H)^+$ 360.3.

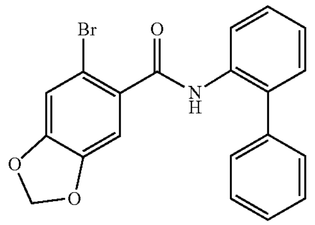 [SMILES: O=C(Nc1ccccc1-c1ccccc1)c1cc2c(cc1Br)OCO2]

Example 49: N-([1,1'-biphenyl]-2-yl)-6-bromobenzo[d][1,3]dioxole-5-carboxamide: The title compound was prepared according to the method of example 48 except that Aniline was replaced with 2-phenyl-aniline. Purification on ISCO (4 g silica column, Ethyl acetate-Hexane, Ethyl acetate %: 0~25%) gave a yellow solid (0.01149 g). $^1H$ NMR (300 MHz, $CDCl_3$): δ 8.46 (d, J=6 Hz, 1H), 7.72 (s, 1H), 7.48-7.36 (m, 6H), 7.20-7.10 (m, 2H), 7.02 (s, 1H), 6.93 (s, 1H), 6.00 (s, 2H, $OCH_2O$). Calculated MS for $C_{20}H_{14}BrNO_3$, 395.02; observed, $(M+H)^+$ 396.4.

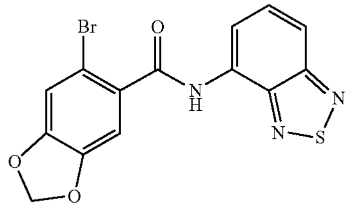 [SMILES: O=C(Nc1cccc2nsnc12)c1cc2c(cc1Br)OCO2]

Example 50: N-(benzo[c][1,2,5]thiadiazol-4-yl)-6-bromobenzo[d][1,3]dioxole-5-carboxamide: 6-bromo-1,3-benzodioxide-5-carboxylic acid (0.0352 g, 0.1436 mmol), 2,1,3-benzothiadiazol-4-amine (0.0265 g, 0.1753 mmol) and (2-(1H-benzotriazol-1-yl)-1,1,3,3-tetramethyluronium hexafluorophosphate) (HBTU, 0.0622 g, 0.1640 mmol) were dissolved in N,N-dimethylformamide (DMF, 1 mL) and treated with N,N-diisopropylethylamine (0.03 mL). The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a yellow solid (0.0191 g, 35.2%). $^1H$ NMR (300 MHz, $CDCl_3$): δ 9.17 (s, 1H), 8.63 (d, J=6 Hz, 1H), 7.75-7.63 (m, 2H), 7.11 (s, 1H), 6.09 (s, 2H, $OCH_2O$). Calculated MS for $C_{14}H_8BrN_3O_3S$, 376.95, observed, $(M+H)^+$ 378.3.

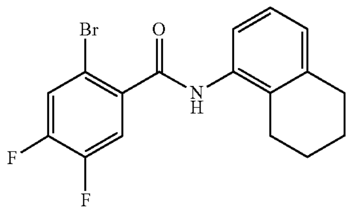 [SMILES: O=C(Nc1cccc2c1CCCC2)c1cc(F)c(F)cc1Br]

Example 51: 2-bromo-4,5-difluoro-N-(5,6,7,8-tetrahydronaphthalen-1-yl)benzamide: 5,6,7,8-tetrahydronaphthalen-1-amine (0.0575 g, 0.3906 mmol) and N,N-diisopropylethylamine (0.08 mL) were dissolved in dichloromethane (1 mL). Then 2-bromo-4,5-difluorobenzoyl chloride (1 mL, 0.1476 mmol/mL) was added to the above solution. The mixture was stirred at 22° C. for 18 hours. Ethyl acetate (20 mL) was added to dilute the mixture and washed with HCl (5 mL, 1M, twice), saturated $NaHCO_3$ solution, and saturated brine, subsequently, and concentrated under vacuum, and purified using normal phase chromatography (4 g Isco silica column, Ethyl acetate-Hexane, 0~20%) gave a white solid (0.0235 g). $^1H$ NMR (300 MHz, $CDCl_3$): δ 7.78 (d, J=6 Hz, 1H), 7.61 (t, J=9 Hz, 1H), 7.52-7.47 (m, 2H), 7.19 (t, J=9 Hz, 1H), 7.00 (d, J=9 Hz, 1H), 2.81 (t, J=6 Hz, 2H), 2.68 (t, J=6 Hz, 2H), 1.87-1.78 (m, 4H). Calculated MS for $C_{17}H_{14}BrF_2NO$, 365.02; observed, $(M+H)^+$ 366.3.

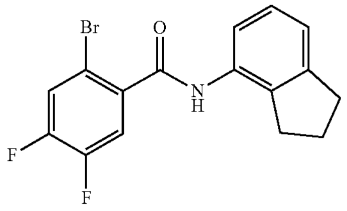 [SMILES: O=C(Nc1cccc2c1CCC2)c1cc(F)c(F)cc1Br]

Example 52: 2-bromo-N-(2,3-dihydro-1H-inden-4-yl)-4,5-difluorobenzamide: The title compound was prepared according to the method of example 51 except that 5,6,7,8-tetrahydronaphthalen-1-amine was replaced with 2,3-dihydro-1H-inden-4-amine. Purification on ISCO (4 g silica column, Ethyl acetate-Hexane, Ethyl acetate %: 0~20%) gave a white solid (0.0356 g). $^1H$ NMR (300 MHz, $CDCl_3$): δ 7.89 (d, J=9 Hz, 1H), 7.67-7.61 (m, 2H), 7.49 (dd, J=9 Hz, 6 Hz, 1H), 7.21 (d, J=6 Hz, 1H), 7.10 (d, J=6 Hz, 1H), 2.99 (t, J=6 Hz, 2H), 2.91 (t, J=6 Hz, 2H), 2.19-2.09 (m, 2H). Calculated MS for $C_{16}H_{12}BrF_2NO$, 351.01; observed, $(M+H)^+$ 352.3.

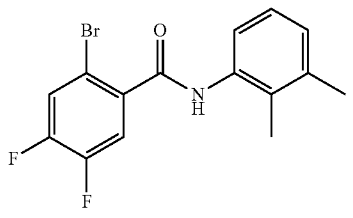 [SMILES: Cc1cccc(NC(=O)c2cc(F)c(F)cc2Br)c1C]

Example 53: 2-bromo-N-(2,3-dimethylphenyl)-4,5-difluorobenzamide: The title compound was prepared according to the method of example 51 except that 5,6,7,8-tetrahydronaphthalen-1-amine was replaced with 2,3-dimethylaniline. Purification on ISCO (4 g silica column, Ethyl acetate-Hexane, Ethyl acetate %: 0~20%) gave a white solid (0.0234 g). $^1$H NMR (300 MHz, $CDCl_3$): δ 7.64-7.47 (m, 4H), 7.17 (t, J=9 Hz, 1H), 7.09 (d, J=6 Hz, 1H), 2.33 (s, 3H, $CH_3$), 2.25 (s, 3H, $CH_3$). Calculated MS for $C_{15}H_{12}BrF_2NO$, 339.01; observed, $(M+H)^+$ 340.3.

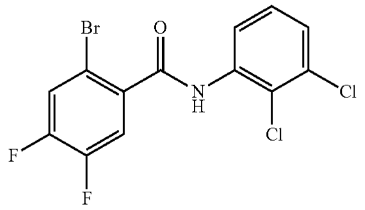 [SMILES: O=C(Nc1cccc(Cl)c1Cl)c1cc(F)c(F)cc1Br]

Example 54: 2-bromo-N-(2,3-dichlorophenyl)-4,5-difluorobenzamide: The title compound was prepared according to the method of example 51 except that 5,6,7,8-tetrahydronaphthalen-1-amine was replaced with naphthalen-1-amine. Purification on ISCO (4 g silica column, Ethyl acetate-Hexane, Ethyl acetate %: 0~20%) gave a white solid (0.0073 g). $^1$H NMR (300 MHz, $CDCl_3$): δ 8.46 (t, J=6 Hz, 1H), 8.34 (s, 1H), 7.63-7.50 (m, 2H), 7.31-7.29 (m, 2H). Calculated MS for $C_{13}H_6BrCl_2F_2NO$, 378.9; observed, $(M+H)^+$ 380.3.

Formulations

The present invention also relates to compositions or formulations which comprise the cyclic GMP-AMP synthase-Stimulator of interferon gene (cGAS-STING) pathway agonists according to the present invention. In general, the compositions of the present invention comprise an effective amount of one or more alkylated imino sugars and salts thereof according to the present invention which are effective for providing glucosidase inhibition; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known antiviral agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound (s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more cyclic GMP-AMP synthase-Stimulator of interferon gene (cGAS-STING) pathway agonists according to the present invention and one or more excipients; from about 0.01 mg to about 100 mg of one or more cyclic GMP-AMP synthase-Stimulator of interferon gene (cGAS-STING) pathway agonists according to the present invention and one or more excipients; and from about 0.1 mg to about 10 mg of one or more cyclic GMP-AMP synthase-Stimulator of interferon gene (cGAS-STING) pathway agonists according to the present invention; and one or more excipients.

Procedures

Cell lines. Human hepatoblastoma cell line HepG2 was obtained from ATCC. Establishment of HepG2-derived cell line stably expressing human STING: HepG2 cells stably expressing wild-type human STING (HepG2/STING), were established by transduction of pCX4bsr retroviral vector (Addgene) containing the corresponding STING cDNA and selection with 10 μg/ml of blasticidin. The HepG2/STING cells were then transduced by pGreenFire ISRE lentivector system (System Biosciences) to generate a reporter cell line HepG2/STING/ISG54Luc that expresses firefly luciferase under the control of an ISG54 promoter. The pGreenFire ISRE reporter lentiviral vector contains four copies of consensus interferon stimulated response element (ISRE) sequences derived from ISG54 ISRE1, which control the expression of both green fluorescent protein (GFP) and firefly luciferase in response to IRF3 activation and IFN stimulation. HepG2/STING/ISG54Luc cells were maintained in Dulbecco's modified minimal essential medium (DMEM)/F12 (Invitrogen) supplemented with 10% fetal bovine serum, 100 U/ml penicillin and 100 μg/ml streptomycin, as well as 400 μg/ml of G418 and 2 μg/ml of puromycin.

ISG54 luciferase reporter assay: HepG2/STING/ISG54Luc reporter cells were seeded in black wall/clear bottom 96-well plates at a density of $4\times10^4$/well in 1 mL of medium overnight. The test compounds were dissolved in DMSO with a stock concentration of 100 mM, and subjected to evaluation of dose-dependent effect on luciferase activity, starting from 100 μM in 2-fold dilution down to 0.78 μM. The experiments were performed in triplex wells.

The firefly luciferase activities were determined at 4 h post treatment with test compounds by using equal volume (1 mL) of Steady-Glo to the culture medium (Promega), followed by luminometry in a TopCounter (Perkin Elmer).

Reporting the ISG54 promotor activation activity. The luciferase activities were converted to fold of induction relative to mock treated control. A dose-dependent curve of luciferase activities (fold of induction) for each test compound was generated using average value from the triplex wells. The activity of the test compounds was reported based on the Minimum Effective Concentration (MinEC5X) to induce 5-fold luciferase activity than that of the mock-treated controls. Specifically, the compounds that dose-dependently enhanced luciferase expression with induction equal or greater than 5-fold at 50 μM concentration in HepG2/STING/ISG54 were considered as active compounds.

TABLE 8

| Concentration required for 5-fold of IFN-□ induction (μM) described herein are: A ≤ 50 μM; 100 ≥ B >50 μM. | |
|---|---|
| 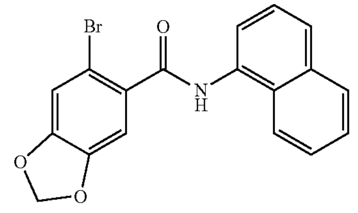 [SMILES: O=C(Nc1cccc2ccccc12)c1cc2c(cc1Br)OCO2] | A |
| 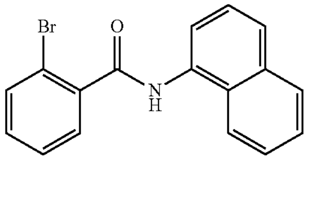 | B |

TABLE 8-continued
| Concentration required for 5-fold of IFN-□ induction (μM) described herein are: A ≤ 50 μM; 100 ≥ B >50 μM. | |
|---|---|
| 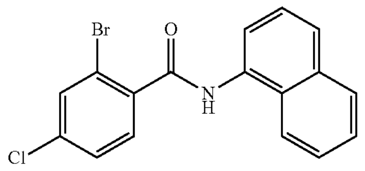 [SMILES: O=C(Nc1cccc2ccccc12)c1ccc(Cl)cc1Br] | A |
| 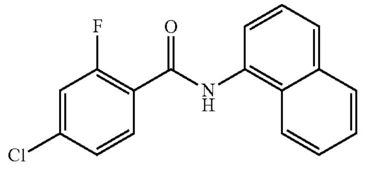 [SMILES: O=C(Nc1cccc2ccccc12)c1ccc(Cl)cc1F] | A |
| 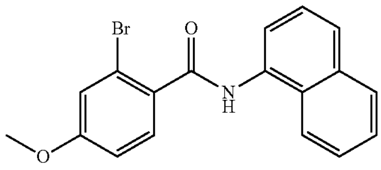 [SMILES: COc1ccc(C(=O)Nc2cccc3ccccc23)c(Br)c1] | A |
| 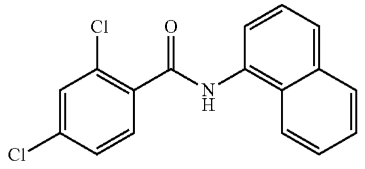 [SMILES: O=C(Nc1cccc2ccccc12)c1ccc(Cl)cc1Cl] | A |
| 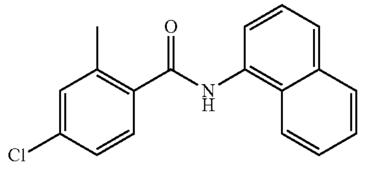 [SMILES: Cc1cc(Cl)ccc1C(=O)Nc1cccc2ccccc12] | A |
| 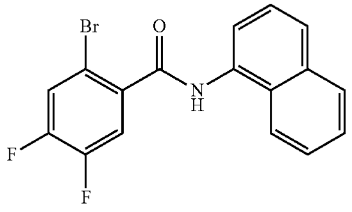 [SMILES: O=C(Nc1cccc2ccccc12)c1cc(F)c(F)cc1Br] | A |
| 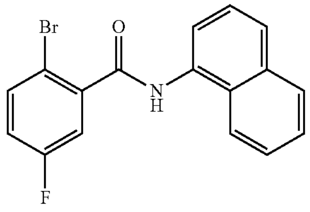 [SMILES: O=C(Nc1cccc2ccccc12)c1cc(F)ccc1Br] | A |
| 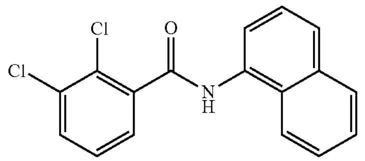 [SMILES: O=C(Nc1cccc2ccccc12)c1cccc(Cl)c1Cl] | A |
TABLE 8-continued
| Concentration required for 5-fold of IFN-□ induction (μM) described herein are: A ≤ 50 μM; 100 ≥ B >50 μM. | |
|---|---|
| 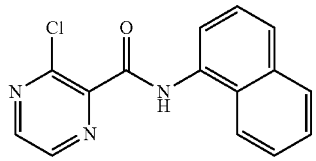 [SMILES: O=C(Nc1cccc2ccccc12)c1nccnc1Cl] | A |
| 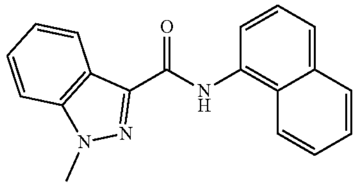 [SMILES: Cn1nc(C(=O)Nc2cccc3ccccc23)c2ccccc21] | A |
| 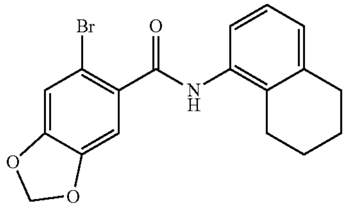 [SMILES: O=C(Nc1cccc2c1CCCC2)c1cc2c(cc1Br)OCO2] | A |
| 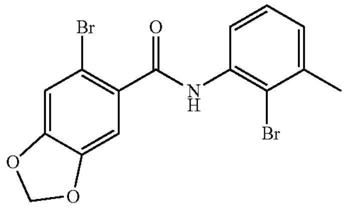 [SMILES: Cc1cccc(NC(=O)c2cc3c(cc2Br)OCO3)c1Br] | A |
| 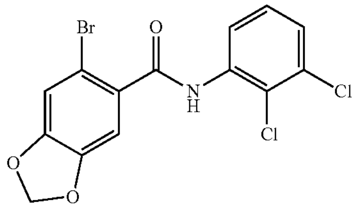 [SMILES: O=C(Nc1cccc(Cl)c1Cl)c1cc2c(cc1Br)OCO2] | A |
| 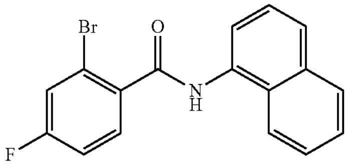 [SMILES: O=C(Nc1cccc2ccccc12)c1ccc(F)cc1Br] | A |
| 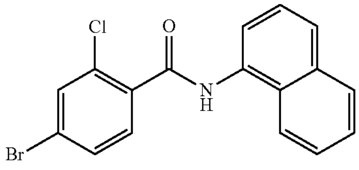 | A |
| 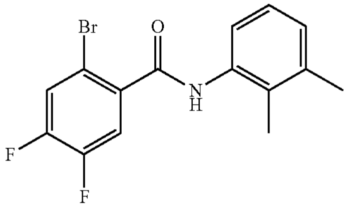 [SMILES: Cc1cccc(NC(=O)c2cc(F)c(F)cc2Br)c1C] | B |

TABLE 8-continued

| Concentration required for 5-fold of IFN-□ induction (μM) described herein are: A ≤ 50 μM; 100 ≥ B >50 μM. | |
|---|---|
| 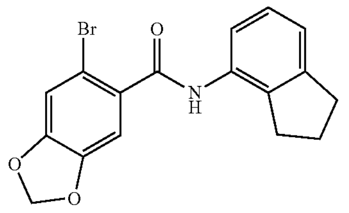 [SMILES: O=C(Nc1cccc2c1CCC2)c1cc2c(cc1Br)OCO2] | A |
| 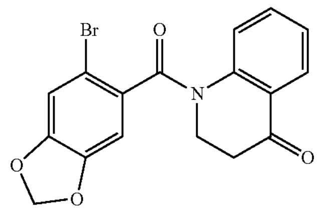 [SMILES: O=C1CCN(C(=O)c2cc3c(cc2Br)OCO3)c2ccccc21] | A |
| 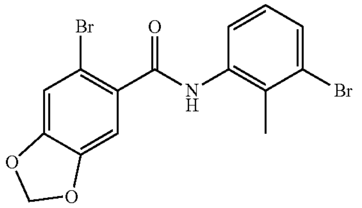 [SMILES: Cc1c(Br)cccc1NC(=O)c1cc2c(cc1Br)OCO2] | A |
| 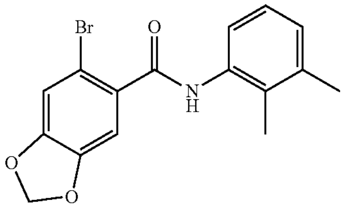 [SMILES: Cc1cccc(NC(=O)c2cc3c(cc2Br)OCO3)c1C] | A |
| 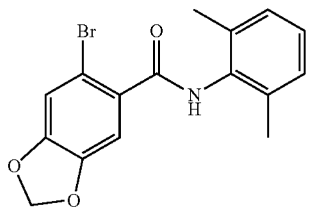 [SMILES: Cc1cccc(C)c1NC(=O)c1cc2c(cc1Br)OCO2] | A |
| 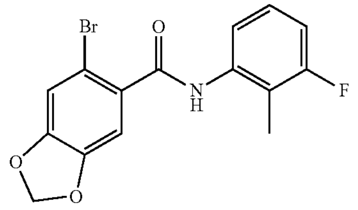 [SMILES: Cc1c(F)cccc1NC(=O)c1cc2c(cc1Br)OCO2] | A |
| 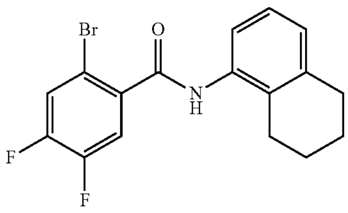 [SMILES: O=C(Nc1cccc2c1CCCC2)c1cc(F)c(F)cc1Br] | A |

TABLE 8-continued

| Concentration required for 5-fold of IFN-□ induction (μM) described herein are: A ≤ 50 μM; 100 ≥ B >50 μM. | |
|---|---|
| 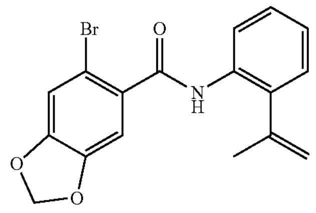 [SMILES: C=C(C)c1ccccc1NC(=O)c1cc2c(cc1Br)OCO2] | A |
| 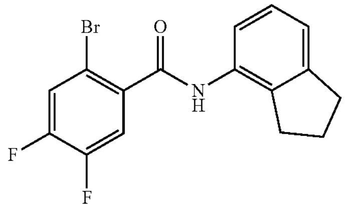 [SMILES: O=C(Nc1cccc2c1CCC2)c1cc(F)c(F)cc1Br] | A |

What is claimed is:

1. A compound having formula (II):

(II)

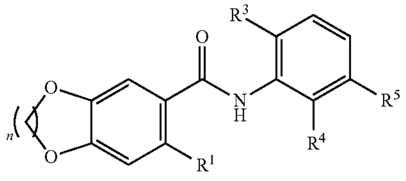

or a hydrate, solvate, pharmaceutically acceptable salt, prodrug or complex thereof, wherein:

$R^1$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

$R^3$ is selected from a group consisting of hydrogen, halogen, optionally substituted $C_{1-6}$ haloalkyl, optionally substituted $C_{1-6}$ alkenyl, $CO_2R^7$, $CONHR^8$, $NHR^9$, $NR^9R^{10}$, $OR^{10}$, cyano, $N_3$, $SO_2R^{11}$, optionally substituted phenyl, optionally substituted heteroaryl, and N-containing monocyclic heterocycloalkyl;

n is 1;

$R^4$ and $R^5$ are taken together with the atom to which they are bound to form an optionally substituted cycloalkane ring having 5 ring atoms;

$R^7$ is selected from a group consisting of hydrogen, optionally substituted $C_{1-4}$ alkyl, optionally substituted $C_3$-$C_7$ cycloalkyl, and optionally substituted phenyl;

$R^8$ is selected from a group consisting of hydrogen, optionally substituted $C_{1-4}$ alkyl, optionally substituted $C_3$-$C_7$ cycloalkyl, and optionally substituted phenyl;

$R^9$ is selected from a group consisting of hydrogen, optionally substituted $C_{1-4}$ alkyl, optionally substituted $C_3$-$C_7$ cycloalkyl, and optionally substituted phenyl, optionally substituted heteroaryl, $COR^{10}$, $SO_2R^{10}$;

$R^{10}$ is selected from a group consisting of hydrogen, optionally substituted $C_{1-4}$ alkyl, optionally substituted $C_3$-$C_7$ cycloalkyl, and optionally substituted phenyl, or two $R^{10}$ units are taken together with the atoms to which they are bound to form a ring having 5-8 ring atoms, or $R^9$ and $R^{10}$ units are taken together with the atoms to which they are bound to form a ring having 5-8 ring atoms;

$R^{11}$ is selected from a group consisting of hydrogen, optionally substituted $C_{1-4}$ alkyl, optionally substituted $C_3$-$C_7$ cycloalkyl, and optionally substituted phenyl.

2. A composition comprising an effective amount of at least one compound according to claim 1.

3. A composition according to claim 2, further comprising at least one excipient.

4. A method of treating a disease associated with dysregulation of the cyclic GMP-AMP synthase-Stimulator of interferon gene (cGAS-STING) pathway wherein said method comprising administering to a subject an effective amount of at least one compound according to the claim 1 to treat the disease.

5. The method of claim 4 wherein the disease associated with dysregulation of the cyclic GMP-AMP synthase-Stimulator of interferon gene (cGAS-STING) pathway is viral infection.

6. The method of claim 4 wherein the disease associated with dysregulation of the cyclic GMP-AMP synthase-Stimulator of interferon gene (cGAS-STING) pathway is cancer.

7. The compound of claim 1, wherein $R^4$ and $R^5$ are taken together with the atom to which they are bound to form a substituted cycloalkane ring having 5 ring atoms.

8. The compound of claim 1, wherein $R^1$ is a halogen.

9. The compound of claim 8, wherein the halogen is bromine.

10. The compound of claim 1, wherein $R^3$ is hydrogen.

* * * * *